(12) United States Patent
Przyborski et al.

(10) Patent No.: US 8,293,803 B2
(45) Date of Patent: Oct. 23, 2012

(54) RETINOID COMPOUNDS AND THEIR USE

(75) Inventors: Stefan Przyborski, Durham (GB); Andrew Whiting, Durham (GB); Todd Marder, Durham (GB)

(73) Assignee: Reinnervate Limited, Durham (GB)

( * ) Notice: Subject to any disclaimer, the term of this patent is extended or adjusted under 35 U.S.C. 154(b) by 357 days.

(21) Appl. No.: 12/439,510

(22) PCT Filed: Aug. 28, 2007

(86) PCT No.: PCT/GB2007/003237
§ 371 (c)(1),
(2), (4) Date: Dec. 22, 2009

(87) PCT Pub. No.: WO2008/025965
PCT Pub. Date: Mar. 6, 2008

(65) Prior Publication Data
US 2010/0093088 A1    Apr. 15, 2010

(30) Foreign Application Priority Data

Aug. 29, 2006 (GB) ................................. 0616961.9
Jan. 31, 2007 (GB) ................................. 0701795.7

(51) Int. Cl.
*A61K 31/07* (2006.01)
*C12N 5/02* (2006.01)

(52) U.S. Cl. ...................................... 514/725; 435/377
(58) Field of Classification Search .................. 514/725; 435/377
See application file for complete search history.

(56) References Cited

U.S. PATENT DOCUMENTS
5,324,840 A    6/1994  Chandraratna

FOREIGN PATENT DOCUMENTS
| EP | 0176034 A | 4/1986 |
| EP | 1612264 A | 1/2006 |
| WO | WO 97/33881 A | 9/1997 |
| WO | WO 99/56740 | 11/1999 |

OTHER PUBLICATIONS

Alvarez, R. et al.: "Both retinoic-acid-receptor and retinoid-X-receptor-dependent signalling pathways mediate the induction of the brown-adipose-tissue-uncoupling-protein-1 gene by retinoids." The Biochem. J., v. 345, pt. 1, (Jan. 1, 2001), p. 91-97.
Åström, A. et al: "Retinoic Acid and Synthetic Analogs Differentially Activate Retinoic Acid Receptor Dependent Transcription." Biochem. and Biophys Res. Comm., v. 173, No. 1, 1990, p. 339-345.
Beard, R. et al: "Synthesis and structure-activity relationships of stilbene retinoid analogs substituted with heteroaromatic carboxylic acids." J. of Med. Chem., v. 38, No. 15, (Jul. 21, 1995), p. 2820-2829.
Dawson, M. I. et al: "Synthesis and pharmacological activity of 6-[(E)-2-(2,6,6-trimethyl-1cyclohexen-1-yl)ethen-1-yl]- and 6-(1,2,3,4-tetrahydro-1,1,4,4-tetra methyl-6-naphthyl)-2-naphthalenecarboxylic acids." J. Med. Chem., v. 26, No. 11, (Nov. 1983), p. 1653-1656.
Gambone C. J. et al: "Unique property of some synthetic retinoids: activation of the aryl hydrocarbon receptor pathway." Mol. Pharm., v. 61, No. 2, (Feb. 2002) p. 334-342.
Hellemans, K., et al: "Differential modulation of rat hepatic stellate phenotype by natural and synthetic retinoids." Hepatology, v. 39, No. 1, (Jan. 2004), p. 97-108.
Kagechika, H., et al: "Retinobenzoic acids. 3. Structure-activity relationships of retinoidal azobenzene-4-carboxylic acids and stilbene-4-carboxylic acids." J. Med. Chem., v. 32, No. 5, (May 1989), p. 1098-1108.
Kistler, A., et al: "Teratogenicity of arotinoids (retinoids) in vivo and in vitro," Arch. of Toxicology, v. 64, No. 8, 1990, p. 616-622.
Lee, H-Y, et al: "Retinoic acid receptor—and retinoid X receptor—selective retinoids activate signaling pathways that converge on AP-1 and inhibit squamous differentiation in human bronchial epithelial cells," Cell Growth & Diff., v. 7, No. 8. (Aug. 1996), p. 997-1004.
Miller, D., et al: "The epithelial differentiating activity in vivo of (E)-4-[2-(5,6,7,8-tetrahydro-5,5,8,8-tetra methyl-2-naphthylenyl)-1-propenyl] benzoic acid and 4,4-difluororetinoic acid," The Biochem. J., v. 227, No. 1, (Apr. 1, 1985, p. 311-316.
Ney, U. M. et al: Antil-Inflammatory effects of synthetic retinoids may be related to their immunomodulatory action, Dermatologica, v. 175, No. suppl. 1, 1987, p. 93-99.
Strickland, S. et al.: "Structure-activity relationships of a new series of retinoidal benzoic acid derivatives as measured by induction of differentiation of murine F9 teratocarcinoma cells and human HL-60 promyelocytic leukemia cells," Cancer Research, v. 43, No. 11, (Nov. 1983), p. 5268-5272.
Zimmermann, B. et al: "Teratogenicity of arotinoid ethyl ester (RO 13-6298) in mice," Teratogenesis, Carcinogenesis, an Mutagenesis, v. 5, No. 6, 1985, p. 415-431.
Chandraratna, R.A.S. et al., "Development of RAR Subtype Selective Retinoids for Dermatological Diseases," European J. of Med. Chem., vol. 30, No. suppl., p. 505S-517S, 1995.
Christie, V.B., et al., "Synthesis and Evaluation of Synthetic Retinoid Derivatives as Inducers of Stem Cell Differentiation," Organic & Biomolecular Chem., vol. 6, No. 19,p. 3497-3507, Oct. 7, 2008.
Liu, S.S, et al., "Systemic Pharmacokinetics of Acetylenic Retinoids in Rats," Drug Metabolism & Disposition, vol. 18, No. 6, p. 1071-1077, Nov. 1, 1999.
Oda, R.M. et al., "Effects of Structural Changes on Retinoid Cytotoxicity in the CHO Clonal Assay," In Vitro Toxicology, vol. 9, No. 2, p. 173-181, 1996.

*Primary Examiner* — Raymond Henley, III
(74) *Attorney, Agent, or Firm* — Morgan, Lewis & Bockius LLP

(57) ABSTRACT

The invention relates to retinoid compounds of the formula (I):

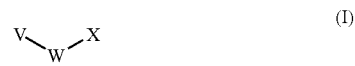

wherein
V is a hydrophobic group;
W is a non-polyenic linker; and
X is a polar group comprising a hydrogen bond donor;
or a salt thereof, and to the use of such compounds in the control of cell differentiation.

12 Claims, 5 Drawing Sheets

RETINOID COMPOUNDS AND THEIR USE

FIELD OF THE INVENTION

The present invention relates to retinoid compounds and their use, for example in cell differentiation.

BACKGROUND OF THE INVENTION

All-trans-retinoic acid (ATRA) and its stereoisomer, 9-cis-retinoic acid (9-cis-RA), are two active metabolites of vitamin A which are known to regulate a broad range of biological processes, including vertebrate development, growth, proliferation and cell differentiation. Retinoids are understood to induce cell differentiation by binding to distinct families of ligand-activated nuclear receptors (RARs) and retinoid X receptors (RXRs).

Naturally occurring retinoids, including ATRA, 9-cis-RA (9CRA) and 13-cis-retinoic acid (13CRA), can be described as chromophores since they selectively absorb light. Such molecules are essentially composed of three structurally distinct regions: a hydrophobic end, a polyene linker and an acidic group. The polyene linker in naturally occurring retinoids is highly conjugated and it is this region that gives it the ability to absorb light (at a frequency of 300-400 nm depending on the solvent). It is due to this feature that these molecules are particularly susceptible to photoisomerisation and can degrade into a mixture of different retinoic acid isomers. The resulting concentration of retinoid levels has also been shown to decrease markedly over time in culture and this could be a consequence of both their degradation and metabolism. Moreover, retinoids such as ATRA are temperature sensitive and are known to oxidise readily.

Isomerisation of ATRA is understood to be an important part of its metabolic pathway because the resulting isomers have different mechanisms of action. This is an important point that is all too often over-looked by users of ATRA in the cell culture laboratory. It has been reported that the isomers of ATRA differentially affect the ability of mammalian stem cells to differentiate along alternative lineages and stated that extreme care should be taken to protect retinoic acids from isomerisation in such experiments (Murayama et al J. Nutr. Sci. Vitaminol 43(167) 1977. This is particularly relevant when the cellular response is determined by the concentration(s) of the isomer(s) present in solution. For example, the induction of the differentiation of pluripotent stem cells using retinoids is quite often variable, resulting in the formation of heterogeneous cultures of cells composed of different proportions of alternative cell types. To reduce such variability in differentiation response and improve reproducibility, it is essential that whatever is used to induce cell differentiation is in the same form and concentration every time it is used. Currently, this cannot be guaranteed when using reagents such as ATRA and its stereoisomers, all of which are light and heat sensitive and are prone to undergo isomerisation under sample preparation conditions, under storage of stock solution conditions and in culture conditions.

It is because the different isomers have diverse effects on cells that some attempts have been made to control ATRA's sensitivity and tendency to isomerise. For example, a number of additives preventing cis-trans interconversions or oxidation of retinoic acids have been evaluated, including bovine serum albumin (BSA), fibrogen, lysozyme, phosphatidylcholine N-ethylmaleimide and vitamin C (Chen et al. J. Am. Chem. Soc. 126 (410) 1995; Wang et al. J Chromatogr 796, 283, 2003). However, the addition of such molecules to cell culture media is not desirable; for example, the use of BSA would not be possible in serum free culture media.

There is a need for improved alternatives to ATRA that do not suffer from the aforementioned stability problems and which can readily be used in cell culture applications.

SUMMARY OF THE INVENTION

The present invention is based, at least in part, on a realisation that, by replacing the polyenic linker of naturally occurring retinoid compounds by a non-polyenic linker, the stability of the compounds can be improved, without a significant impact on the biological activity of the compounds. Conjugated polyene linkers are susceptible to photoisomerisation; replacing the polyene framework with non-isomerising functions improves the stability of the compounds.

Accordingly, a first aspect of the present invention concerns the use of a retinoid compound to control cell differentiation, wherein the compound comprises a hydrophobic group and a polar group comprising a hydrogen bond donor, wherein said groups are separated by a non-polyenic linker. Methods of controlling cell differentiation are also provided.

The retinoid compounds of the invention may be used to modulate the differentiation of stem cells in a manner resembling naturally occurring retinoids. The compounds may direct cell differentiation in a more uniform manner, reducing the variation and heterogeneity of alternative differentiating cell types compared to routine stem cell culture using ATRA. With the benefit of improved stability, the use of these reagents may reduce cellular heterogeneity in cultures of differentiating cells. Stable, synthetic modulators of cell differentiation offer distinct advantages over existing technology and will be of significant value to biotechnologists.

The application of this technology to systems both with and without a methyl group (e.g. in 6a versus 6b), is important because it allows control of relative rotational orientation of the aryl and vinyl groups which has important implications for the control of conformation as a design principle for developing receptor-selective retinoid analogues. Compounds of formulae 6 are efficacious in modulating cell differentiation. Compounds of formulae 6aii and 6bi are also efficacious in modulating cell differentiation and are particularly stable.

The tetrahydronaphthalene core of the aryl-alkenyl boronate 5a has already attracted attention as a basic sub-unit for deriving retinoid derivatives that have been applied as potent retinoid X-receptor ligands which cause apoptosis in leukaemia cells, and this substructure is a flexible intermediate for the development of novel, active retinoids for differentiation of stem cells.

The compounds of the invention can exist in different forms, such as free acids, free bases, esters and other prodrugs, salts and tautomers, for example, and the disclosure includes all variant forms of the compounds.

Features, integers, characteristics, compounds, chemical moieties or groups described in conjunction with a particular aspect, embodiment or example of the invention are to be understood to be applicable to any other aspect, embodiment or example described herein unless incompatible therewith.

DETAILED DESCRIPTION OF THE INVENTION

Polyenic

Figure 1:
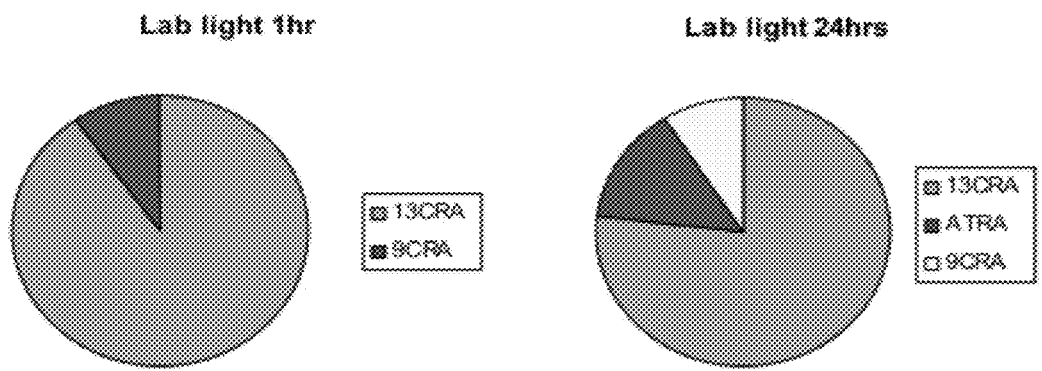
FIG. 1 is a pie chart showing the relative levels of the natural retinoids in samples of 13CRA exposed to 1 hour (left) and 24 hours (right) laboratory light conditions (in November or December)

The terms "polyene" and "polyenic" as used herein include reference to aliphatic moieties comprising two or more conjugated carbon-carbon double bonds.

Hydrocarbyl

The term "hydrocarbyl" as used herein includes reference to moieties consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g cyclopropylmethyl); cycloalkyl (e.g. cyclopropyl, cyclobutyl, cyclopentyl or cyclohexyl); alkenyl (e.g. 2-butenyl); alkynyl (e.g. 2-butynyl); aryl (e.g. phenyl, naphthyl or fluorenyl) and the like.

Alkyl

The terms "alkyl" and "$C_{1-6}$ alkyl" as used herein include reference to a straight or branched chain alkyl moiety having 1, 2, 3, 4, 5 or 6 carbon atoms. This term includes reference to groups such as methyl, ethyl, propyl (n-propyl or isopropyl), butyl (n-butyl, sec-butyl or tert-butyl), pentyl, hexyl and the like. In particular, alkyl may have 1, 2, 3 or 4 carbon atoms.

Alkenyl

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

Alkynyl

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

Alkoxy

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

Cycloalkyl

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

Aryl

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

Carbocyclyl

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, a 5- or 6-membered ring, which may be saturated or unsaturated. A carbocyclic moiety is, for example, selected from cyclopropyl, cyclobutyl, cyclopentyl, cyclohexyl, norbornyl, bicyclo [2.2.2]octyl, phenyl, naphthyl, fluorenyl, azulenyl, indenyl, anthryl and the like.

Heterocyclyl

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

Heterocycloalkyl

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like.

Heteroaryl

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

Halogen

The term "halogen" as used herein includes reference to F, Cl, Br or I. In a particular, halogen may be F or Cl, of which F is more common.

Substituted

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or unsubstituted.

It will, of course, be understood that substituents are only at positions where they are chemically possible, the person skilled in the art being able to decide (either experimentally or theoretically) without inappropriate effort whether a particular substitution is possible. For example, amino or hydroxy groups with free hydrogen may be unstable if bound to carbon atoms with unsaturated (e.g. olefinic) bonds. Additionally, it will of course be understood that the substituents described herein may themselves be substituted by any substituent, subject to the aforementioned restriction to appropriate substitutions as recognised by the skilled man.

Independently

Where two or more moieties are described as being "each independently" selected from a list of atoms or groups, this means that the moieties may be the same or different. The identity of each moiety is therefore independent of the identities of the one or more other moieties.

Compounds

The invention provides the use of a retinoid compound to control cell differentiation, wherein the compound comprises a hydrophobic group and a polar group comprising a hydrogen bond donor, wherein said groups are separated by a non-polyenic linker.

Preferably the non-polyenic linker is less susceptible to photoisomerisation than a polyenic group. Preferably still the linker may comprise an unsaturated group.

In a preferred use according to the invention the retinoid compound is of the formula (I):

wherein
V is a hydrophobic group;
W is a non-polyenic linker; and
X is a polar group comprising a hydrogen bond donor;
or a salt thereof.

In a preferred use according to the invention V is a group of the formula (I):

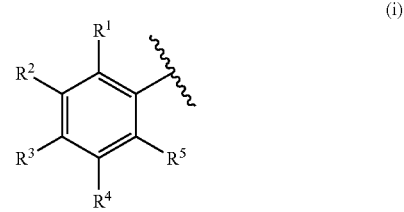

wherein
$R^1$, $R^2$, $R^3$, $R^4$ and $R^5$ are each independently selected from hydrogen, $R^6$, hydrocarbyl optionally substituted with 1, 2, 3, 4 or 5 $R^6$, and —$(CH_2)_k$-heterocyclyl optionally substituted with 1, 2, 3, 4 or 5 $R^6$,
wherein each $R^6$ is independently selected from halogen, trifluoromethyl, cyano, nitro, oxo, =$NR^7$, —$OR^7$, —$C(O)R^7$, —$C(O)OR^7$, —$OC(O)R^7$, —$S(O)_lR^7$, —$N(R^7)R^8$, —$C(O)N(R^7)R^8$, —$S(O)_lN(R^7)R^8$ and $R^9$;
$R^7$ and $R^8$ are each independently hydrogen or $R^9$;
$R^9$ is selected from hydrocarbyl and —$(CH_2)_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;
k is 0, 1, 2, 3, 4, 5 or 6;
l is 0, 1 or 2; and
m is 0, 1, 2, 3, 4, 5 or 6;
or one or more $R^1$ and $R^2$, $R^2$ and $R^3$, $R^3$ and $R^4$, and $R^4$ and $R^5$ taken together with the atoms to which they are attached form a carbocycle or a heterocycle, optionally substituted with one or more $R^6$.

In a further preferred use according to the invention only one or two of $R^1$, $R^2$, $R^3$, $R^4$ and $R^5$ is hydrogen.

In a preferred use according to the invention V is a group of one of the following formulae:

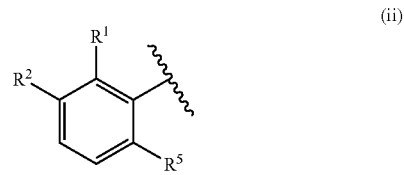

(iii)

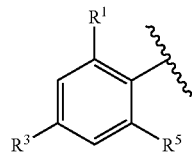

(iv)

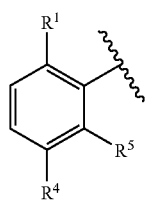

(v)

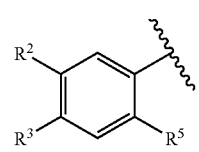

(vi)

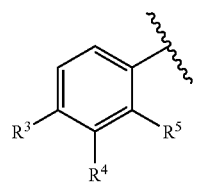

(vii)

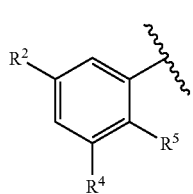

wherein each of said R groups is other than hydrogen.

Preferably V is a group of the formula (v). In a preferred compound of the invention V is a group of the formula (viii):

(viii)

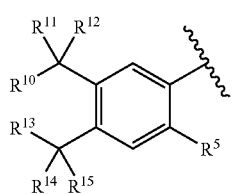

wherein $R^{10}$, $R^{11}$, $R^{12}$, $R^{13}$, $R^{14}$ and $R^{15}$ are each independently selected from hydrogen, $R^6$, hydrocarbyl optionally substituted with 1, 2, 3, 4 or 5 $R^6$, and —$(CH_2)_k$-heterocyclyl optionally substituted with 1, 2, 3, 4 or 5 $R^6$;

or $R^{10}$ and $R^{13}$ form a $C_{1-4}$ alkylene linker optionally substituted with 1, 2, 3, 4 or 5 $R^6$.

Preferably $R^{10}$, $R^{11}$, $R^{12}$, $R^{13}$, $R^{14}$ and $R^{15}$ are each independently selected from hydrogen and $C_{1-6}$ alkyl.

In a preferred use according to the invention V is a group of the formula (ix):

(ix)

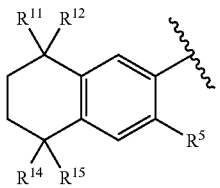

Preferably $R^{11}$, $R^{12}$, $R^{14}$ and $R^{15}$ are each independently hydrogen or $C_{1-6}$ alkyl.

Preferably still $R^{11}$, $R^{12}$, $R^{14}$ and $R^{15}$ are each methyl.

In a preferred use according to the invention $R^5$ is selected from hydrogen, $R^6$, hydrocarbyl optionally substituted with 1, 2, 3, 4 or 5 $R^6$, and —$(CH_2)_k$-heterocyclyl optionally substituted with 1, 2, 3, 4 or 5 $R^6$.

In a further preferred use according to the invention $R^5$ is selected from hydrogen, halogen, $C_{1-6}$ alkyl optionally substituted with 1, 2, 3, 4 or 5 $R^6$, —$OR^7$, —$S(O)_iR^7$ and —$N(R^7)R^8$.

In a further preferred use according to the invention $R^5$ is selected from hydrogen and $C_1$, $C_2$, $C_3$ and $C_4$ alkyl.

In a yet further preferred use according to the invention $R^5$ is hydrogen or methyl.

Preferably W is a linker having from 2 to 10 in-chain atoms, for example, a linker having 2, 3, 4, 5, 6, 7 or 8 in-chain atoms.

Preferably W is an unsaturated group. W may comprise one or more, for example two, unsaturated aliphatic or aromatic groups for example one or more groups independently selected from $C_{2-6}$ alkenylene, $C_{2-6}$ alkynylene, arylene and heteroarylene, any of which is optionally substituted with 1, 2, 3, 4 or 5 $R^6$, wherein $R^6$ is as defined herein.

W may comprise one or more groups independently selected from $C_{2-6}$ alkenylene, $C_{2-6}$ alkynylene, phenylene and naphthylene, any of which is optionally substituted with 1, 2, 3, 4 or 5 $R^6$.

W may comprise one or more groups independently selected from $C_{2-6}$ alkynylene, phenylene and naphthylene, any of which is optionally substituted with 1, 2, 3, 4 or 5 $R^6$.

W may comprise one or more groups independently selected from $C_{2-6}$ alkenylene, $C_{2-6}$ alkynylene, phenylene and naphthylene, any of which is optionally substituted with 1, 2, 3, 4 or 5 $R^6$.

In a preferred use according to the invention W is the linker -A-B-, wherein A is linked to V and B is linked to X, and wherein A and B are each independently selected from $C_{2-6}$ alkenylene, $C_{2-6}$ alkynylene, arylene and heteroarylene, any of which is optionally substituted with 1, 2, 3, 4 or 5 $R^6$. The linker may be selected from alkenylene;
alkynylene;
-phenylene-alkenylene-;
-alkenylene-phenylene-;
-phenylene-alkynylene-;
-alkynylene-phenylene-; and
naphthylene;
any of which is optionally substituted with 1, 2, 3, 4 or 5 $R^6$.

Preferably the linker is selected from -phenylene-alkenylene-; -alkynylene-phenylene and naphthylene any of which is optionally substituted with 1, 2, 3, 4 or 5 $R^6$.

Preferably W is a linker selected from:
propylene;
ethynylene;
-phenylene-propylene-;
-ethynylene-phenylene-; and
naphthylene;
any of which is optionally substituted with 1, 2, 3, 4 or 5 $R^6$.

In one embodiment W is the linker -phenylene-propylene-.

In a further embodiment W is the linker -ethynylene-phenylene-.

In a preferred embodiment of the invention W is not -prop-2-ylene-phenylene, wherein the prop-2-ylene group is attached to the hydrophobic group.

In a preferred use according to the invention X comprises —C(O)Z, wherein Z comprises a hydrogen bond donor. Preferably X is —C(O)Z. Z may be selected from —OH, —C(O)OH, O($C_{1-6}$ alkyl), —$NH_2$ and NHOH. Preferably Z is selected from —OH, $OCH_3$ and NHOH.

In a preferred use according to the invention the compound is of the formula (II):

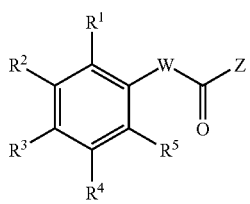

(II)

wherein
$R^1$, $R^2$, $R^3$, $R^4$ and $R^5$ are as defined herein; and
Z is as defined herein;
or a salt thereof.

Preferably the compound is of the formula (III):

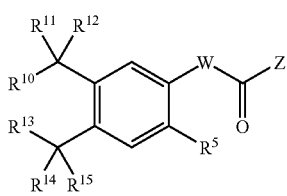

(III)

wherein $R^{10}$, $R^{11}$, $R^{12}$, $R^{13}$, $R^{14}$ and $R^{15}$ are as defined herein.

Preferably still the compound is of the formula (IV):

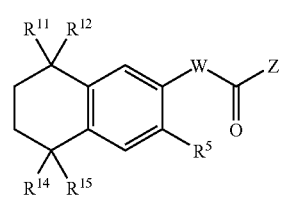

(IV)

In a preferred use according to the invention $R^{11}$, $R^{12}$, $R^{14}$ and $R^{15}$ are each independently hydrogen or $C_{1-6}$ alkyl.

In a preferred use according to the invention the compound is of one of the following formulae:

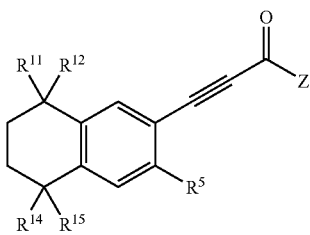

(V)

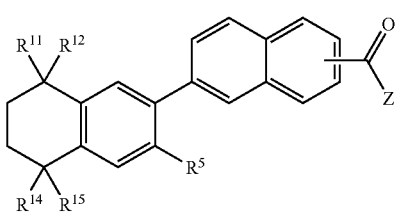

(VI)

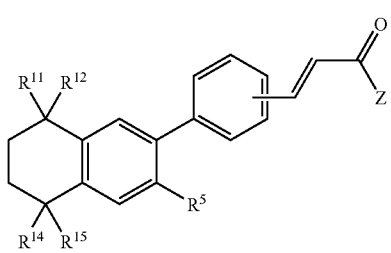

(VII)

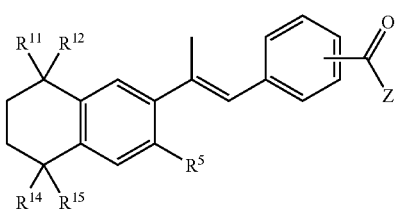

(VIII)

In a preferred use according to the invention the compound is of the formulae (V), (VI) or (VII). Preferably still the compound is of formulae (V) or (VII).

In a preferred embodiment the compound is of one of the following formulae:

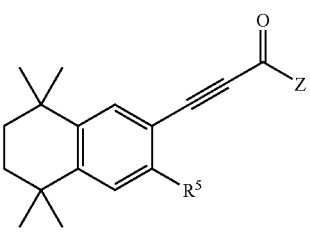

(IX)

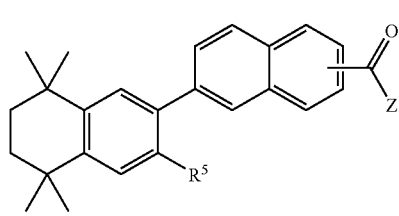

(X)

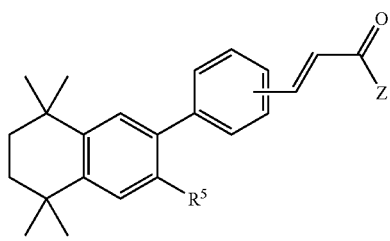

(XI)

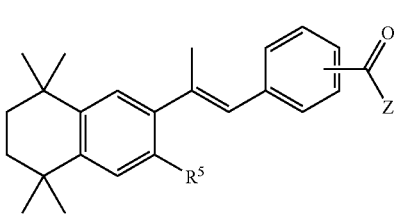

(XII)

In a preferred use according to the invention the compound is of the formulae (IX), (X) or (XI). Preferably still the compound is of formulae (IX) or (XI).

Preferably $R^5$ is hydrogen or methyl.

In a preferred use according to the invention the compound is 6, 10, 11, 12 or 13 as described herein for example compound 10, 11 or 12 as described herein.

In a preferred use according to the invention the compound is of formula (IX)

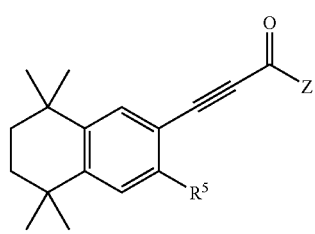

(IX)

wherein $R^5$ and Z are as defined herein. Preferably $R^5$ is H or methyl. Preferably Z is OH, $OCH_3$ or NHOH.

In a preferred use according to the invention the compound is of the formula (X)

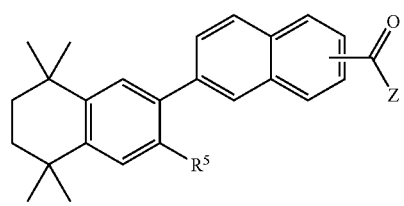

(X)

wherein $R^5$ and Z are as defined herein. Preferably $R^5$ is H or methyl. Preferably $R^5$ is methyl. Preferably Z is OH.

In a preferred use according to the invention the compound is of formula (XI)

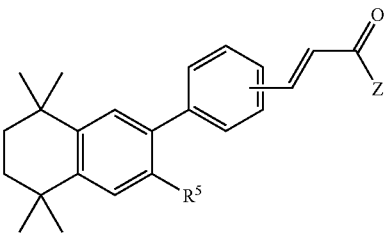

(XI)

wherein $R^5$ and Z are as defined herein. Preferably $R^5$ is H or methyl. Preferably Z is OH.

In a preferred use according to the invention the compound is of formula (XII)

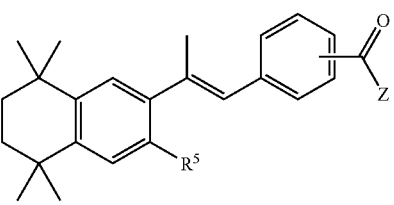

(XII)

wherein $R^5$ and Z are as defined herein. Preferably Z is $OCH_3$. Preferably $R^5$ is methyl when Z is not OH.

In a preferred use according to the invention the compound is not a compound of the formula (XIII):

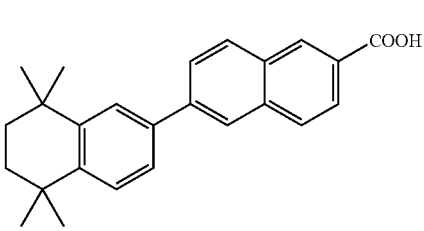

(XIII)

In a preferred use according to the invention the compound is not a compound of the formula (XIV):

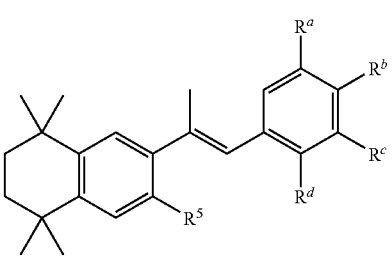

(XIV)

wherein $R^a$, $R^b$, $R^c$, $R^d$ and $R^5$ are as follows:

| $R^5$ | $R^a$ | $R^b$ | $R^c$ | $R^d$ |
|---|---|---|---|---|
| H | H | —C(O)OH | H | H |
| H | H | H | —C(O)OH | H |
| H | H | H | H | H |
| $CH_3$ | H | —C(O)OH | H | H |
| $C_2H_5$ | H | —C(O)OH | H | H |
| n-$C_3H_7$ | H | —C(O)OH | H | H |
| i-$C_3H_7$ | H | —C(O)OH | H | H |
| —$OCH_3$ | H | —C(O)OH | H | H |
| $CH_3$ | H | H | —C(O)OH | H |
| H | H | —C(O)OH | H | H |
| H | H | —$CH_2$OH | H | H |
| H | H | —$CO_2C_2H_5$ | H | H |
| H | H | —$SO_2^-Na^+$ | H | H |
| H | H | —$SO_3^-Na^+$ | H | H |
| H | H | —$SO_2C_2H_5$ | H | H |
| H | H | H | H | —C(O)OH |
| H | $CH_3$ | —C(O)OH | H | H |
| H | H | —C(O)OH | H | $CH_3$ |

In a further aspect the invention provides a retinoid compound as defined herein independent of use.

By way of illustration, a compound of the invention may be prepared according to the following general Schemes:

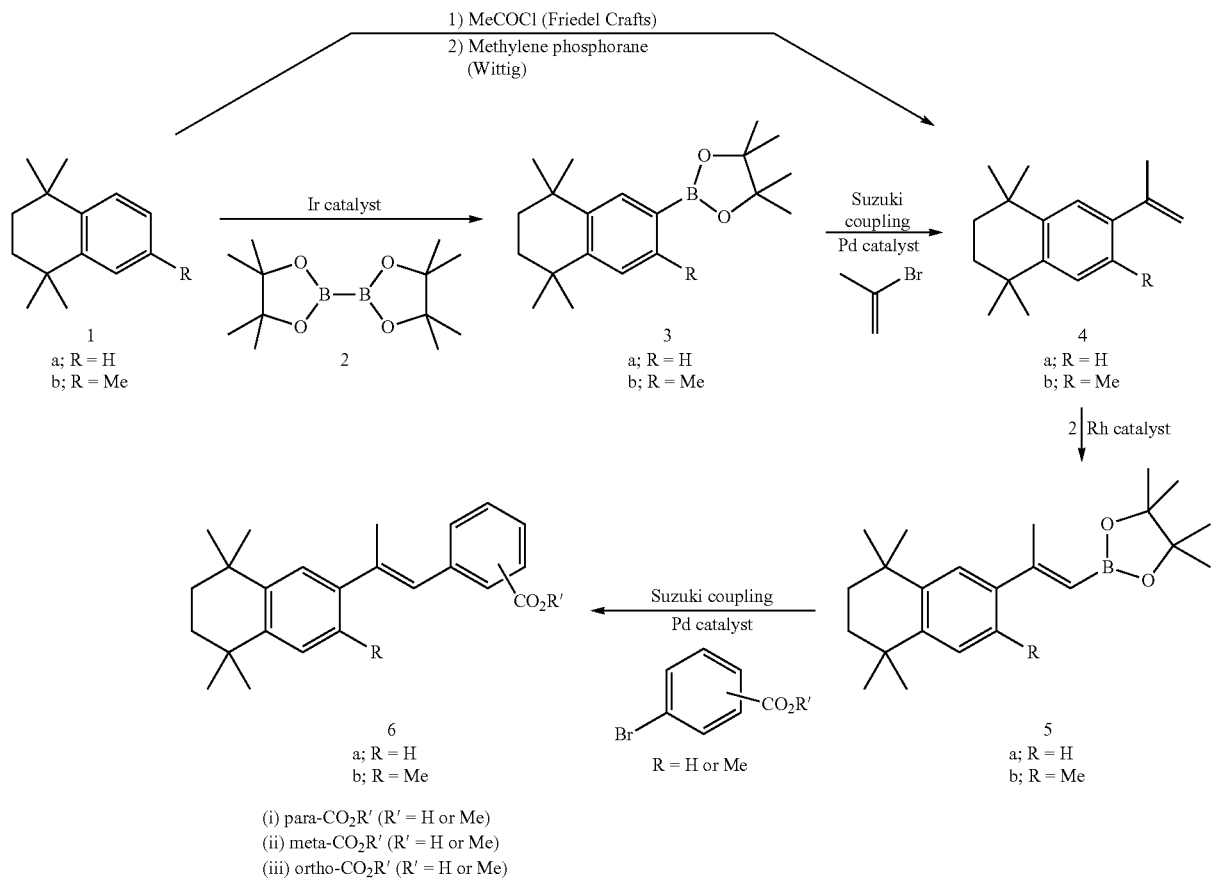

According to Scheme 1, structures of type 1 can be converted to 5 and onto analogues 6 via the sequence of efficient metal-catalysed reactions, including two C—H activation steps in the presence of a catalyst. In the case of the preparation of 4b, this compound may be efficiently prepared in two steps from 1b, via a Friedel-Crafts acetylation and Wittig methylation sequence.

Similarly, this type of approach has been extended to produce compounds 10 and 11 via Scheme 2 as shown below. While 10a(iii) exists as a mixture of acetylene and ene-lactone derivatives, 10a(i) and (ii) are also useful probes for examining differentiation process.

Scheme 2
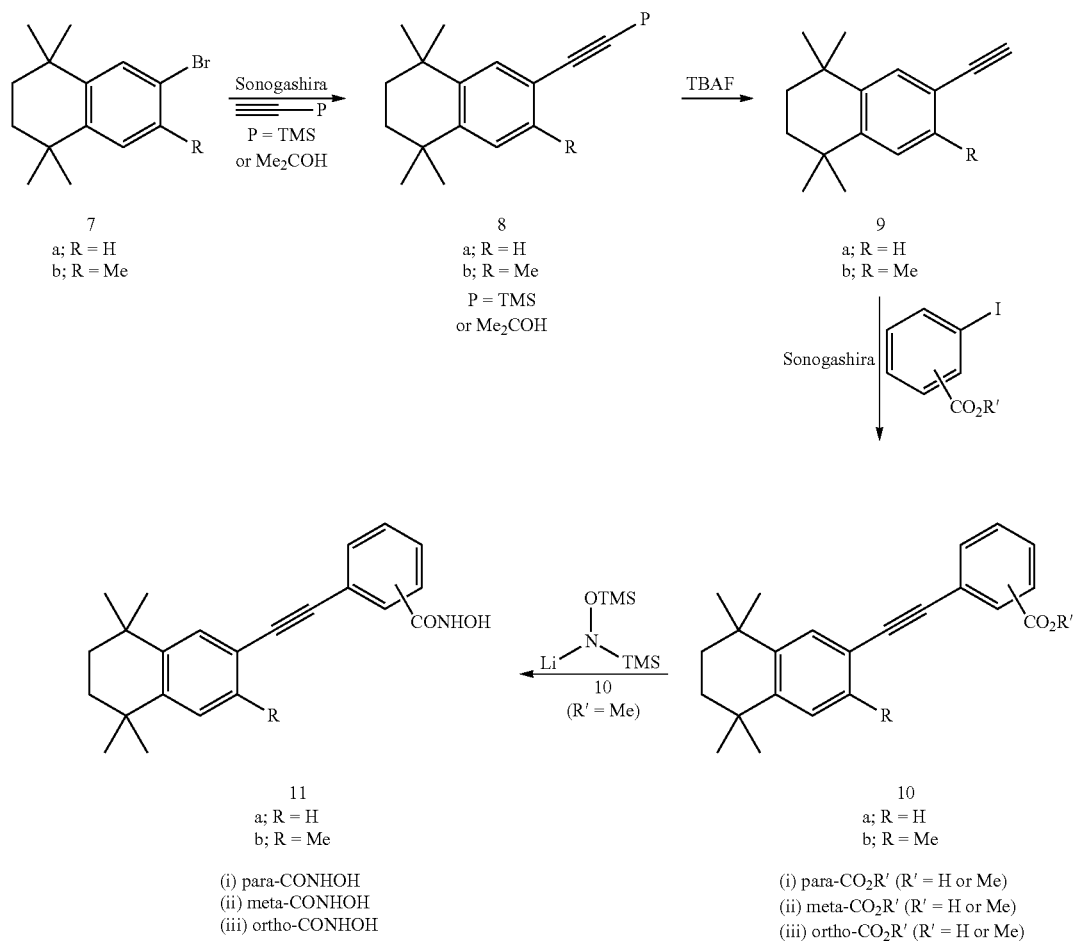
Scheme 3
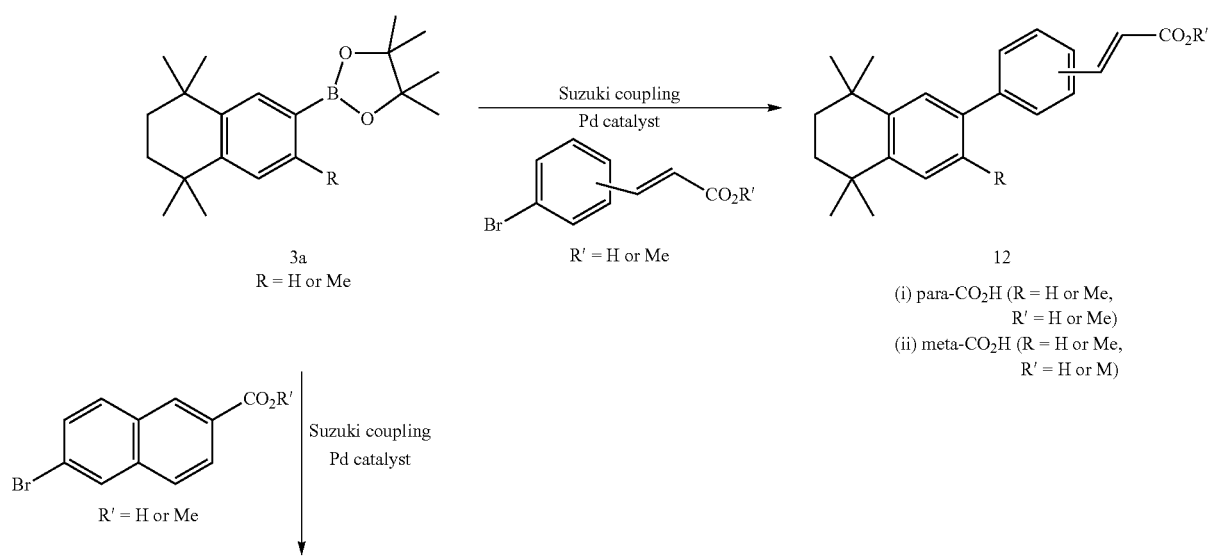

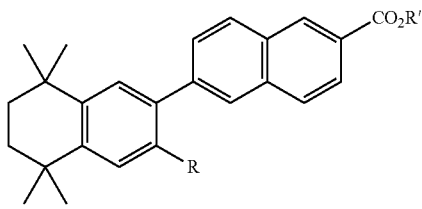

13
R = H or Me, R' = H or M

A similar strategy can be used to access related systems 12 and 13, as outlined in Scheme 3. In this case, the borylated intermediate 3a can be directly converted using palladium-mediated cross-coupling to derive cinnamate analogues 12, or it can be readily converted to the naphthyl system 13.

It will be understood that the processes detailed above are solely for the purpose of illustrating the invention and should not be construed as limiting. A process utilising similar or analogous reagents and/or conditions known to one skilled in the art may also be used to obtain a compound of the invention.

Any mixtures of final products or intermediates obtained can be separated on the basis of the physico-chemical differences of the constituents, in a known manner, into the pure final products or intermediates, for example by chromatography, distillation, fractional crystallisation, or by the formation of a salt if appropriate or possible under the circumstances.

Some groups mentioned herein (especially those containing heteroatoms and conjugated bonds) may exist in tautomeric forms and all these tautomers are included in the scope of the disclosure. More generally, many species may exist in equilibrium, as for example in the case of organic acids and their counterpart anions; a reference herein to a species accordingly includes reference to all equilibrium forms thereof.

The compounds of the disclosure may also contain one or more asymmetric carbon atoms and may therefore exhibit optical and/or diastereoisomerism. All diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid or amine followed by separation of the diastereomeric derivatives by conventional means (e.g. HPLC, chromatography over silica). All stereoisomers are included within the scope of the disclosure. Where a single enantiomer or diastereomer is disclosed, the disclosure also covers the other enantiomers or diastereomers, and also racemates; in this regard, particular reference is made to the specific compounds listed herein.

Geometric isomers may also exist in the compounds of the present disclosure. The present disclosure contemplates the various geometric isomers and mixtures thereof resulting from the arrangement of substituents around a carbon-carbon double bond and designates such isomers as of the Z or E configuration, wherein the term "Z" represents substituents on the same side of the carbon-carbon double bond and the term "E" represents substituents on opposite sides of the carbon-carbon double bond.

Use

In a preferred use according to the invention there is provided the use of a retinoid compound as defined herein in the differentiation of a stem cell into at least one differentiated cell type.

In a preferred embodiment of the invention said stem cell is non-human totipotent stem cell for example a mouse totipotent cell.

In a preferred embodiment of the invention said stem cell is a pluripotent stem cell, preferably a human pluripotent stem cell.

In an alternative preferred embodiment of the invention said stem cell is a multipotent stem cell.

In a preferred embodiment of the invention said multipotent stem cell is selected from the group consisting of: haemopoietic stem cell, neural stem cell, bone stem cell, muscle stem cell, mesenchymal stem cell, epithelial stem cell (derived from organs such as the skin, gastrointestinal mucosa, kidney, bladder, mammary glands, uterus, prostate and endocrine glands such as the pituitary), ectodermal stem cell, mesodermal stem cell or endodermal stem cell (for example derived from organs such as the liver, pancreas, lung and blood vessels).

According to a further aspect of the invention there is provided a method to induce the differentiation of a stem cell comprising the steps of:
i) forming a preparation of stem cells in a cell culture medium suitable for maintaining said stem cells wherein said culture medium comprises a retinoid compound as defined herein; and
ii) cultivating said stem cells in conditions that allow their differentiation into at least one differentiated cell type.

In a preferred method of the invention said stem cell is not a totipotent stem cell. Preferably said stem cell is human.

In a preferred method of the invention said differentiated cell is selected from the group consisting of a keratinocyte, a fibroblast (e.g. dermal, corneal, intestinal mucosa, oral mucosa, bladder, urethral, prostate, liver), an epithelial cell (e.g. dermal, corneal, intestinal mucosa, oral mucosa, bladder, urethral, prostate, liver), a neuronal glial cell or neural cell, a hepatocyte, a mesenchyma cell, a muscle cell (cardiomyocyte or myotube cell), a kidney cell, a blood cell (e.g. CD4+ lymphocyte, CD8+ lymphocyte), a pancreatic cell, or an endothelial cell.

In a preferred method of the invention the method takes place in the presence of visible and/or UV light, temperatures not exceeding 50° C. (for example −80° C. up to 50° C., typically −20° C. up to about 40° C.) and/or oxidative reagents for example air or DMSO.

The method of the invention may take place ex vivo, in vivo or in vitro.

A further aspect of the invention provides a method of irradiating a compound, which comprises irradiating a retinoid compound as defined herein with visible or UV light.

A further aspect of the invention provides a retinoid compound as defined herein for use in therapy.

A yet further aspect of the invention provides a pharmaceutical formulation comprising a retinoid compound as defined herein and a pharmaceutically acceptable carrier or excipient.

In a further aspect of the invention there is provided the use of a retinoid compound as defined herein in the manufacture of a medicament for the treatment of a disease or condition that would benefit from retinoid therapy. Disease or conditions that may benefit from retinoid therapy include cancer (e.g. neural neoplasms), skin disorders such as acne, skin wounds e.g. burns, UV damage, aging skin.

EXAMPLES

Example 1

Synthesis of Compounds

Compounds 6, 10, 11, 12 and 13 were prepared according to Schemes 1, 2 and 3 supra.

Experimental

All reactions were carried out under a dry nitrogen atmosphere using standard Schlenk techniques or in an Innovative Technology Inc. System 1 double-length glove box. Glassware was oven dried before transfer into the glove box.

Hexane and THF were dried over sodium/benzophenone and acetonitrile was dried over $CaH_2$ and all were distilled under nitrogen. The solvent 1,4-dioxane was degassed by 3 freeze-pump-low-cycles. Toluene was dried and deoxygenated by passage through columns of activated alumina and BASF-R311 catalyst under Ar pressure using a locally modified version of the Innovative Technology, Inc. SPS-400 solvent purification system.

The compound 1,1,4,4-tetramethyl-1,2,3,4-tetrahydronaphthalene was purchased from Avocado Chemical Company and was dried over $CaH_2$ and distilled. [Ir(μ-Cl)(COE)$_2$]$_2$ (Ent et al, *Inorg. Synth.* 1990, 28, 90), trans-[Rh(Cl)(CO)(PPh$_3$)$_2$] (Evans et al, *Inorg. Synth.* 1966, 8, 215; and McLeverty et al, *Inorg. Synth.* 1968, 11, 99) and Wittig reagent (Ph$_3$PMe$^+$I$^-$), were synthesised by literature procedures, B$_2$pin$_2$ was supplied as gifts by Frontier Scientific Inc. and NetChem Inc. Hydrochloric acid was obtained from Fisher Scientific and all other compounds were obtained from Aldrich Chemical Company, tested for purity by GC/MS and used without further purification.

NMR spectra were recorded at ambient temperature on Varian Inova 500 ($^1$H, $^{13}$C{$^1$H}, HSQC), Varian C500 ($^1$H, $^{13}$C{$^1$H}, HSQC, HMBC), Varian Unity 300 ($^{11}$B and $^{11}$B{$^1$H}) and Bruker AC200 ($^{13}$C{$^1$H}) instruments. Proton and carbon spectra were referenced to external SiMe$_4$ via residual protons in the deuterated solvents or solvent resonance respectively and $^{11}$B NMR spectra were referenced to external BF$_3$.OEt$_3$. Elemental analyses were conducted in the Department of Chemistry at the University of Durham using an Exeter Analytical Inc. CE-440 Elemental Analyser.

GC-MS analyses were performed on a Hewlett-Packard 5890 Series II gas chromatograph equipped with a 5971 mass selective detector and a 7673 autosampler or on an Agilent 6890 Plus GC equipped with a 5973N MSD and an Anatune Focus robotic liquid handling system/autosampler. A fused silica capillary column (10 m or 12 m cross-linked 5% phenylmethylsilicone) was used, and the oven temperature was ramped from 50° C. to 280° C. at a rate of 20° C./min. UHP grade helium was used as the carrier gas. The screw-cap autosampler vials used were supplied by Thermoquest Inc. and were fitted with Teflon/silicone/Teflon septa and 0.2 ml micro inserts.

NMR data confirmed the identity of each of the following compounds:

Intermediate 3a: 6-Bpin-1,1,4,4-tetramethyl-1,2,3,4-tetrahydronaphthalene

In a nitrogen-filled glove box, to a solution of [Ir(Cl)(COE)$_2$]$_2$ (23.8 mg, 26.6×10$^{-3}$ mmol, 2.5 mol %) and dtbpy (14.3 mg, 53.2×10$^{-3}$ mmol, 5 mol %) in 2 ml of THF was added a mixture of B$_2$pin$_2$ (270 mg, 1.06 mmol, 1 equiv.) and 1,1,4,4-tetramethyl-1,2,3,4-tetrahydronaphthalene 1a (200 mg, 1.06 mmol) in 3 ml of THF (5 ml total volume). The mixture was shaken vigorously to ensure complete mixing, transferred to ampoules sealed with a Teflon Young's tap and heated at 80° C. After 3 d, the mixture was analyzed by GC/MS, and then the solvent was removed in vacuo. The product can be chromatographed on silica gel (hexane:DCM, 50:50) to yield 242 mg (72%) of product 3a; M.p.=104-106° C.;

Intermediate 4a: 6-isopropenyl-1,1,4,4-tetramethyl-1,2,3,4-tetrahydronaphthalene In a nitrogen-filled glove box, to an ampoule sealed with a Teflon Young's tap containing a solution of 6-Bpin-1,1,4,4-tetramethyl-1,2,3,4-tetrahydronaphthalene 3a (50 mg, 159×10$^{-3}$ mmol), and 2-bromopropene (19.1 mg, 159×10$^{-3}$ mmol) in 1 ml of 1,4-dioxane was added a solution of Pd(OAc)$_2$ (1.78 mg, 7.95×10$^{-3}$ mmol) and PPh$_3$ (4.15 mg, 15.9×10$^{-3}$ mmol) (2 ml total volume) of 1,4-dioxane. To this mixture, 1 ml of aq. K$_3$PO$_4$ (101 mg, 477.5×10$^{-3}$ mmol) was added under nitrogen, and then the reaction mixture was heated at 80° C. After 3 h, in situ GC/MS showed conversion of the boronate ester compound to the alkene product. The product was extracted with ethyl acetate, dried over MgSO$_4$, and chromatographed on silica gel (hexane:DCM 60:40) to yield 66 mg (90%) of 4a.

Intermediate 5a: 6-(2-Bpin-1-methyl-vinyl)-1,1,4,4-tetramethyl-1,2,3,4-tetrahydronaphthalene In a nitrogen-filled glove box, to a solution of trans-[Rh(Cl)(CO)(PPh$_3$)$_2$] (12.1 mg, 17.5×10$^{-3}$ mmol, 5 mol %) in 2 ml of a mixture of toluene/acetonitrile (3:1) was added 89.2 mg (351×10$^{-3}$ mmol, 1 equiv.) of B$_2$pin$_2$ and 6-isopropenyl-1,1,4,4-tetramethyl-1,2,3,4-tetrahydronaphthalene 4a (80 mg, 0.350 mmol) in 2 ml of 3:1 toluene/acetonitrile solvent (4 ml total solvent volume). The mixture was shaken vigorously to ensure complete mixing, transferred to ampoules sealed with a Teflon Young's tap and then heated to 80° C. The reaction was monitored by GC/MS. After 3 d, the solvent was removed in vacuo and redissolved in a mixture of hexane/DCM (60:40), and then chromatographed on silica gel (hexane/DCM, 60:40) to yield 98 mg (80%) of 7; M.p. 128-130° C.;

Compound 6a(i): TTNPB, 4-[2-(5,5,8,8-Tetramethyl-5,6,7,8-tetrahydro-naphthalen-2-yl)-propenyl]-benzoic acid (R'=H)

Pd(dppf)Cl$_2$, (33 mg, 0.04 mmol), 5a (142 mg, 0.4 mmol) and 4-iodobenzoic acid (121 mg, 0.4 mmol) where dissolved in DMF (15 cm³) and added to a Schlenk tube in a glove box. $K_3PO_4$ (200 mg, 0.8 mmol) in degassed $H_2O$ (3 cm³) was added via cannula and the mixture heated until GCMS analysis showed complete consumption of 6a(i). Dilute $HCl_{(aq.)}$ (2 cm³) was added and the mixture extracted with DCM (3×10 cm³); the organic phase was washed with dilute $HCl_{(aq.)}$ (3×10 cm³), dried over $MgSO_4$ and concentrated in vacuo.

4-[2-(5,5,8,8-Tetramethyl-5,6,7,8-tetrahydronaphthalen-2-yl)-propenyl]-benzoic acid methyl ester 6a(i) (R'=Me)

In a dry, $N_2$ filled glovebox, $Pd(dppf)Cl_2$ (33 mg, 0.04 mmol), 4,4,5,5-tetramethyl-2-[2-(5,5,8,8-tetramethyl-5,6,7,8-tetrahydronaphthalen-2-yl)-propenyl]-[1,3,2]-dioxaborolane 5a (0.40 g, 1.1 mmol), 4-iodobenzoic acid methyl ester (0.24 g, 0.9 mmol), $K_3PO_4.2H_2O$ (0.57 g, 2.3 mmol) and degassed DMF (15 mL) were added to a thick walled glass tube sealed with a Young's tap. The tube was attached to a Schlenk line and degassed $H_2O$ (3 mL) was added via cannula. The mixture was heated at 80° C. until GCMS analysis showed complete consumption of the starting materials (2 d). Dilute $HCl_{(aq.)}$ (2 mL) was added and the mixture was extracted with DCM (3×10 mL). The organic phase was washed with dilute $HCl_{(aq.)}$ (3×10 mL), dried over $MgSO_4$ and concentrated in vacuo. The mixture was filtered through a silica plug with hexane and then 10% DCM/hexanes and the solvent was removed in vacuo. Recrystallisation from hot EtOH gave the product 6a(i) (R'=Me) as a fluffy, white powder (0.28 g, 84%); mp 137-139° C.

3-[2-(5,5,8,8-Tetramethyl-5,6,7,8-tetrahydronaphthalen-2-yl)-propenyl]-benzoic acid methyl ester 6a(ii) (R'=Me)

In a dry, $N_2$ filled glovebox, $Pd(dppf)Cl_2$ (33 mg, 0.04 mmol), 4,4,5,5-tetramethyl-2-[2-(5,5,8,8-tetramethyl-5,6,7,8-tetrahydronaphthalen-2-yl)-propenyl]-[1,3,2]-dioxaborolane 5a (0.40 g, 1.1 mmol), 3-iodobenzoic acid methyl ester (0.24 g, 0.9 mmol), $K_3PO_4.2H_2O$ (0.57 g, 2.3 mmol) and degassed DMF (15 mL) were added to a thick walled glass tube sealed with a Young's tap. The tube was attached to a Schlenk line and degassed $H_2O$ (3 mL) was added via cannula. The mixture was heated at 80° C. until GCMS analysis showed complete consumption of the starting materials (2 d). Dilute $HCl_{(aq.)}$ (2 mL) was added and the mixture was extracted with DCM (3×10 mL). The organic phase was washed with dilute $HCl_{(aq.)}$ (3×10 mL), dried over $MgSO_4$ and concentrated in vacuo. The mixture was filtered through a silica plug with hexane and then 10% DCM/hexanes and the solvent removed in vacuo. Recrystallisation from hot EtOH gave the product as a fluffy, white powder 6a(ii) (R'=Me) (0.25 g, 75%); mp 86-88° C.

Intermediate: 2,5-dichloro-2,5-dimethylhexane

Conc. HCl (37% v/v, d=1.18, 250 ml) was added carefully to 2,5-dimethyl-2,5-hexanediol (20 g, 137 mmol) in a 500 ml conical flask. The mixture was stirred for 24 h and then filtered and the precipitate was washed 3×200 ml with water. The white crystals were redissolved in diethylether and washed with 100 ml water, and then dried over $MgSO_4$. The solvent was removed in vacuo to give 2,5-dichloro-2,5-dimethylhexane 12.9 g (50%) as a white solid; M.p.=62-64° C.

Intermediate 1b: Synthesis of 1,1,4,4,6-pentamethyl-1,2,3,4-tetrahydronaphthalene To a 250 ml round bottomed flask fitted with a magnetic stirring bar and reflux condenser were added 2,5-dichloro-2,5-dimethylhexane (10 g, 54.5 mmol), toluene (10 g, 110 mmol), and 50 ml of DCM. To this vigorously stirred solution was slowly added $AlCl_3$ (100 mg 0.75 mmol) which resulted in rapid evolution of gaseous HCl. The reaction mixture was stirred at room temperature for 30 min followed by reflux for an additional 15 min to give a red solution. After cooling, 10 ml of 20% aqueous HCl was added to the stirred solution, and the reaction mixture turned clear/white. The organic layer was washed with water and extracted with 2×100 ml of hexane, dried over $MgSO_4$, filtered, and concentrated. Kugelrohr distillation (40-100° C., $3\times10^{-4}$ torr) gave an analytically pure sample of 1b (10.5 g, 92%); M.p. 30-32° C.

Intermediate: 1-(3,5,5,8,8-pentamethyl-5,6,7,8-tetrahydronaphthalene-2-yl)-ethanone To a 250 ml three-necked round bottomed flask fitted with a magnetic stirring bar and a reflux condenser containing acetyl chloride (2.3 g, 29.7 mmol) and 50 ml of DCM was added 1,1,4,4,6-pentamethyl-1,2,3,4-tetrahydronaphthalene 1b (5 g, 24.8 mmol) followed by slow addition (ca. 0.5 g portions) of $AlCl_3$ (7.5 g, 56.2 mmol). The brown mixture was stirred for 30 min and then heated at reflux for 15 min. Additional $AlCl_3$ (1-2 g) was necessary to effect the completion of the reaction. The cooled reaction mixture was poured into 200 ml of vigorously stirred ice water followed by acidification with 20% aqueous hydrochloric acid 50 ml and addition of 100 ml of ethyl acetate. Stirring was continued until the organic layer was yellow 15 min. The organic layer was extracted with ethyl acetate (2×100 ml), dried over $MgSO_4$, filtered and concentrated in vacuo. Kugelrohr distillation (80-120° C., $3\times10^{-4}$ torr) gave an analytically pure sample of 1-(3,5,5,8,8-pentamethyl-5,6,7,8-tetrahydronaphthalene-2-yl)ethanone 5.31 g (88%) as a white solid; m.p. 54-56° C.

Intermediate 4b: Synthesis of 6-isopropenyl-1,1,4,4,7-pentamethyl-1,2,3,4-tetrahydronaphthalene In a nitrogen-filled glove box, to 250 ml round bottomed flask fitted with a magnetic stirring bar containing 1-(3,5,5,8,8-pentamethyl-5,6,7,8-tetrahydronaphthalene-2-yl)ethanone (0.5 g, 2.05 mmol) and 50 ml of dry THF was added [$^+PPh_3MeI^-$] (1.24 g, 3.07 mmol), followed by $^tBuOK$ (343 g, 3.06 mmol). The mixture was stirred at room temperature. After 24 h, in situ GC/MS analysis showed complete conversion of the carbonyl compound to the alkene product. The mixture was filtered to remove the salt. The solvent was removed in vacuo and the resulting solid was redissolved in hexane and then cooled in the refrigerator for 24 h to crystallise the $PPh_3O$. The mixture was filtered and cooled again to remove additional $PPh_3O$. This step has to be repeated at least 4 times to remove all of the $PPh_3O$. Finally, the solvent was removed in vacuo to obtain the pure alkene. Alternatively, a faster method of purification, after removal of the salt by filtration, involves concentration in vacuo and then Kugelrohr distillation (100-140° C., $3\times10^{-4}$ torr), which gave an analytically pure sample of 4a (396 mg, 80%); m.p. 39-40° C.

Intermediate 5b: 6-(2-Bpin-1-methyl-vinyl)-1,1,4,4,7-pentamethyl-1,2,3,4-tetrahydro naphthalene In a nitrogen-filled glove box, to a solution of trans-[Rh(Cl)(CO)(PPh_3)_2] (28.5 mg, $41.3\times10^{-3}$ mmol) in 2 ml of a mixture of toluene/acetonitrile (3:1) was added $B_2pin_2$ (201 mg, 0.79 mmol) and 6-isopropenyl-1,1,4,4,7-pentamethyl-1,2,3,4-tetrahydronaphthalene 4b (200 mg, $826\times10^{-3}$ mmol) in 2 ml of 3:1 toluene/acetonitrile (4 ml total solvent volume).

The mixture was shaken vigorously to ensure complete mixing, transferred to ampoules sealed with a Teflon Young's tap and then heated to 80° C. The reaction was monitored by in situ GC/MS. After 3 d, the solvent was removed in vacuo and the resulting solid was redissolved in a mixture of hexane/DCM (60:40), and then chromatographed on silica gel eluting with hexane/DCM (60:40) to yield 151 mg (50%) of product 5b as a white solid; M.p.=78-80° C.

Intermediate 7a: 6-Bromo-1,1,4,4-tetramethyl-1,2,3,4-tetrahydronaphthalene

To a solution of 1,1,4,4-tetramethyl-1,2,3,4-tetrahydronaphthalene 1a (10.0 g, 53.0 mmol) in DCM (60 cm$^3$) at 0° C. under $N_2$ was added $Br_2$ (15.58 g, 97.5 mmol). $BF_3.Et_2O$ (8.27 g, 58.3 mmol) in DCM (10 cm$^3$) was added dropwise over 2 h. The reaction mixture was diluted with 40/60 EtOAc/hexane (150 cm$^3$) and washed with saturated $Na_2SO_3$ solution (100 cm$^3$), saturated $NaHCO_3$ solution (100 cm$^3$), and $H_2O$ (100 cm$^3$). The organic layer was dried over $MgSO_4$, filtered and the solvents removed in vacuo to give a dark brown oil. Kugelrohr distillation (120° C., 8×10$^{-3}$ mbar) gave 7a as pale yellow crystals (11.02 g, 77.8%); M.p. 43° C.

Intermediate 7b: 6-Bromo-1,1,4,4,7-pentamethyl-1,2,3,4-tetrahydronaphthalene

To a solution of 1,1,4,4,6-pentamethyl-1,2,3,4-tetrahydronaphthalene 1b (4.00 vg, 19.78 mmol) in DCM (40 cm$^3$) at 0° C. under $N_2$ was added $Br_2$ (5.69 g, 35.60 mmol), $BF_3.Et_2O$ (3.08 g, 21.76 mmol) in DCM (10 cm$^{-3}$) was added dropwise over the course of 2 h. The reaction mixture was stirred for 1 h then diluted with 40/60 EtOAc/hexane (150 cm$^3$) and washed with saturated $Na_2SO_3$ solution (100 cm$^3$), saturated $HCO_3$ solution (100 cm$^3$), and $H_2O$ (100 cm$^3$). The organic layer was dried over $MgSO_4$, filtered and the solvents removed to give 7b as a white, fluffy powder (4.98 g, 89.5%); M.p. 91° C.

Intermediate 8a: 2-Methyl-4-(5,5,8,8-tetramethyl-5,6,7,8-tetrahydronaphthalen-2-yl)but-3-yn-2-ol (P=dimethylcarbinol)

$PdCl_2$ (0.331 g, 1.87 mmol), $Cu(OAc)_2$ (0.274 g, 1.87 mmol), 7a (5.0 g, 18.71 mmol), and $PPh_3$ (2.45 g, 9.35 mmol) were placed in a 500 cm$^3$ Schlenk flask and the flask evacuated and back filled with $N_2$ gas three times. Dry, degassed triethylamine (150 cm$^3$) was added via canula and 2-methyl-but-3-yn-2-ol (4.72 g, 56.13 mmol) was added via syringe. The solution was stirred under $N_2$ at 70° C. for 3 days. The solvent was removed in vacuo and the residue dissolved in hexane, filtered through a silica gel plug with hexane and then 10% EtOAC/hexane. The EtOAC/hexane solution was washed with dilute $HCl_{(aq.)}$ solution (100 cm$^3$), dried over $MgSO_4$ and the solvent removed to give 8a (P=dimethylcarbinol) as an off white solid (2.25 g, 45%); M.p. 107° C.

Intermediate 8a (P=TMS): Trimethyl-(5,5,8,8-tetramethyl-5,6,7,8-tetrahydro-naphthalen-2-ylethynyl)-silane $PdCl_2$ (0.55 g, 3.1 mmol), $Cu(OAc)_2$ (0.62 g, 3.1 mmol), 7a (8.3 g, 31.0 mmol), and $PPh_3$ (4.06 g, 15.53 mmol) were placed in a 500 cm$^3$ Schlenk flask under $N_2$. Dry, degassed triethylamine (150 cm$^3$) was added via cannula and TMSA (6.09 g, 62.1 mmol) added via syringe. The solution was stirred under $N_2$ at 70° C. overnight until GCMS analysis showed the reaction to be complete (18 h). The solvent was removed in vacuo and the residue dissolved in hexane, filtered through a silica plug with hexane and dried over $MgSO_4$. Removal of the solvent in vacuo gave 8a (P=TMS) as a thick orange oil (7.42 g, 84%) which also contained approximately 10% of TMS diyne and other TMS bearing impurities; m/z (EI-MS) 284 (25%, M$^+$), 269 (100%, Me loss).

Intermediate 9a: 6-Ethynyl-1,1,4,4-tetramethyl-1,2,3,4-tetrahydronaphthalene

To a solution of 2-methyl-4-(5,5,8,8-tetramethyl-5,6,7,8-tetrahydronaphthalen-2-yl)but-3-yn-2-ol 8a (P=dimethylcarbinol) (7.42 g, 26.1 mmol) in 100 cm$^3$ of 1:5 toluene/MeOH, was added freshly powdered KOH (2.92 g, 52.3 mmol). The solution was stirred until GCMS analysis showed the reaction to be complete (18 h). 1:1 hexane/$H_2O$ (100 cm$^3$) was added to separate the polar and non polar solvents. The mixture was washed with dilute $HCl_{(aq.)}$ solution (100 cm$^3$) then water (2×100 cm$^3$). The organic layer was separated, dried over $MgSO_4$ and the solvents removed in vacuo to give 9a as a thick orange oil (4.97 g, 90%).

Compound 10a(i): 4-(5,5,8,8-Tetramethyl-5,6,7,8-tetrahydro-naphthalen-2-ylethynyl)benzoic acid (R'=H)

CuI (0.0164 g, 0.0321 mmol), 4-iodobenzoic acid (0.797 g, 3.21 mmol) and $Pd(PPh_3)_2Cl_2$ (0.0225 g, 0.0321 mmol) were placed in a 250 cm$^3$ Schlenk flask under $N_2$ and 9a (1.224 g, 5.77 mmol) was added. Dry, degassed $Et_3N$ (150 cm$^3$) was added via cannula and the reaction mixture was stirred under $N_2$ for 3 days. The volume of $Et_3N$ was reduced by 50% in vacuo and the remaining mixture diluted with $Et_2O$ (100 cm$^3$), washed with 5% $HCl_{(aq.)}$ solution (3×80 cm$^3$) and brine (3×80 cm$^3$) before being dried over $MgSO_4$. Removal of the solvent on a rotary evaporator and drying in vacuo yielded the crude product. Purification by silica gel chromatography (hexane/$Et_2O$ gradient elution) gave 10a(i) which was recrystallised from hexane to give an off white powder (0.30 g, 28%); M.p. 254-256° C.

Compound 6b(i): 4-[2-(3,5,5,8,8-Pentamethyl-5,6,7,8-tetrahydro-naphthalen-2-yl)propenyl]benzoic acid (R'=H)

Pd(dppf)$Cl_2$, (33 mg, 0.04 mmol), 5b (150 mg, 0.4 mmol) and 4-iodobenzoic acid (121 mg, 0.4 mmol) where dissolved in DMF (15 cm$^3$) and added to a Schlenk tube in a glove box. $K_3PO_4$ (200 mg, 0.8 mmol) in degassed $H_2O$ (3 cm$^3$) was added via cannula and the mixture heated until GCMS analysis showed complete consumption of 5b. Dilute $HCl_{(aq.)}$ (2 cm$^3$) was added and the mixture extracted with DCM (3×10 cm$^3$); the organic phase was washed with dilute $HCl_{(aq.)}$ (3×10 cm$^3$), dried over $MgSO_4$ and concentrated in vacuo.

4-[2-(3,5,5,8,8-Pentamethyl-5,6,7,8-tetrahydronaphthalen-2-yl)-propenyl]-benzoic acid methyl ester 6b(i) (R'=Me)

In a dry, $N_2$ filled glovebox, Pd(dppf)$Cl_2$ (28 mg, 0.03 mmol), 4,4,5,5-tetramethyl-2-[2-(3,5,5,8,8-pentamethyl-5,6,7,8-tetrahydronaphthalen-2-yl)-propenyl]-[1,3,2]-dioxaborolane 5b (0.30 g, 0.82 mmol), 4-iodobenzoic acid methyl ester (0.18 g, 0.68 mmol), $K_3PO_4.2H_2O$ (0.42 g, 1.7 mmol) and degassed DMF (15 mL) were added to a thick walled glass tube sealed with a Young's tap. The tube was attached to a Schlenk line and degassed H$_2$O (3 mL) was added via cannula. The mixture was heated at 80° C. until GCMS analysis showed complete consumption of the starting materials (2 d). Dilute HCl$_{(aq.)}$ (2 mL) was added and the mixture was extracted with DCM (3×10 mL). The organic phase was washed with dilute HCl$_{(aq.)}$ (3×10 mL), dried over MgSO$_4$ and concentrated in vacuo. The mixture was filtered through a silica plug with hexane and then 10% DCM/hexanes and the solvent was removed in vacuo. Recrystallisation from hot EtOH gave the product 6b(i) (R'=Me) as a fluffy, white powder (0.22 g, 86%); mp 137-139° C.

3-[2-(3,5,5,8,8-Pentamethyl-5,6,7,8-tetrahydronaphthalen-2-yl)-propenyl]-benzoic acid methyl ester 6b(ii) (R'=Me)

In a dry, N$_2$ filled glovebox, Pd(dppf)Cl$_2$ (285 mg, 0.03 mmol), 4,4,5,5-tetramethyl-2-[2-(3,5,5,8,8-pentamethyl-5,6,7,8-tetrahydronaphthalen-2-yl)-propenyl]-[1,3,2]-dioxaborolane 5b (0.30 g, 0.82 mmol), 3-iodobenzoic acid methyl ester (0.18 g, 0.68 mmol), K$_3$PO$_4$.2H$_2$O (0.42 g, 1.7 mmol) and degassed DMF (15 mL) were added to a thick walled glass tube sealed with a Young's tap. The tube was attached to a Schlenk line and degassed H$_2$O (3 cm$^3$) was added via cannula. The mixture was heated at 80° C. until GCMS analysis showed complete consumption of the starting materials (2 d). Dilute HCl$_{(aq.)}$ (2 mL) was added and the mixture was extracted with DCM (3×10 mL). The organic phase was washed with dilute HCl$_{(aq.)}$ (3×10 mL), dried over MgSO$_4$ and concentrated in vacuo. The mixture was filtered through a silica plug with hexane and then 10% DCM/hexanes and the solvent was removed in vacuo. Recrystallisation from hot EtOH gave the product 6b(ii) (R'=Me) as a fluffy, white powder (0.22 g, 86%); mp 91-92° C.

4-(3,5,5,8,8-Pentamethyl-5,6,7,8-tetrahydronaphthalen-2-ylethynyl)-benzoic acid methyl ester 10b(i) (R'=Me)

Pd(PPh$_3$)$_2$Cl$_2$ (29 mg, 0.042 mmol), CuI (8 mg, 0.004 mmol), 4-iodobenzoic acid methyl ester (1.1 g, 4.2 mmol) and 6-ethynyl-1,1,4,4,7-pentamethyl-1,2,3,4-tetrahydronaphthalene 9b (1.0 g, 4.4 mmol) were placed in a 250 mL Schlenk flask under N$_2$. Dry, degassed Et$_3$N (100 mL) was added via cannula. The reaction was stirred under N$_2$ for 3 d. The solvent was removed in vacuo and the residue filtered through a SiO$_2$ plug eluting with hexane (200 mL) and 50/50 DCM/hexane (200 mL). The DCM/hexane fraction was evaporated in vacuo to give a pale brown solid. Recrystallisation from EtOH gave to 10b(i) (R'=Me) white needles (0.12 g, 77%); mp 135-137.

3-(3,5,5,8,8-Pentamethyl-5,6,7,8-tetrahydronaphthalen-2-ylethynyl)-benzoic acid methyl ester 10b(ii) (R'=Me)

Pd(PPh$_3$)$_2$Cl$_2$ (29 mg, 0.042 mmol), CuI (8 mg, 0.0042 mmol), 3-iodobenzoic acid methyl ester (1.1 g, 4.21 mmol) and 6-ethynyl-1,1,4,4,7-pentamethyl-1,2,3,4-tetrahydronaphthalene 9b (1.0 g, 4.42 mmol) were placed in a 250 mL Schlenk flask under N$_2$. Dry, degassed Et$_3$N (100 mL) was added via cannula. The reaction was stirred under N$_2$ for 3 d. The solvent was removed in vacuo and the residue filtered through a SiO$_2$ plug eluting with hexane (200 mL) and 50/50 DCM/hexane (200 mL). The DCM/hexane fraction was evaporated in vacuo to give a pale brown solid. Recrystallisation from EtOH to gave 10b(ii) (R'=Me) white needles (0.11 g, 71%); mp 115-117.

Compound 11a(ii): 3-(5,5,8,8-Tetramethyl-5,6,7,8-tetrahydronaphthalen-2-ylethynyl)benzohydroxamic acid N,O-Bis(trimethylsilyl)hydroxylamine (0.2 ml, 0.92 mmol) and dry THF (2 ml) was cooled to −78° C. with stirring under an argon atmosphere. n-BuLi (0.37 ml of a 2.5M solution in hexanes) was added slowly to the stirring solution allowed to re-cool to −78° C. 10a(ii) (160 mg, 0.462 mmol) was added to the stirring solution (still under argon). This was stirred at −78° C. for 2 hrs, and then allowed to warm to room temperature and stirred overnight. The solution was then heated to reflux, becoming cloudy (formation of product?) for 5 hrs. The reaction was then quenched with 10% HCl (~4 ml) and stirred for an hour. H$_2$O (4 ml) was added to the solution and then extracted with Ethyl Acetate (3×15 ml). The combined organics were washed with brine (7 ml), dried (MgSO$_4$), filtered and solvent removed to afford a crude oil (170 mg). 140 mg of the mixture was separated by silica gel chromatography to afford 11a(ii) as a pale yellow solid (55 mg, 40%). Recrystallisation of the solid from hot acetonitrile gave a brilliant white solid.

Compound 12(i) (R=H, R'=H)

In a nitrogen atmosphere, 3a (515 mg, 1.6 mmol), 4-bromocinnamic acid (396 mg, 1.7 mmol, 1.1 equiv.), Pd(PPh$_3$)$_4$ (58.7 mg, 51 μmol) and Ba(OH)$_2$.8H$_2$O (1.26 g, 4.0 mmol) were dissolved in a degassed mixture of N,N-dimethylacetamide/purified water (5:1, 17 ml). The solids did not dissolve completely. The reaction was heated at 80° C. in a sealed tube for 3 days when the reaction was quenched with dilute hydrochloric acid (2 ml) and extracted with EtOAc (50 ml). The organic phase was washed with brine (1×10 ml) and dilute hydrochloric acid (3×20 ml); the combined aqueous washings were back-extracted with EtOAc (2×50 ml). The combined organic layers were dried over MgSO$_4$, filtered and concentrated in vacuo. The crude off-white product was purified by flash silica gel chromatography (THF as eluant), and recrystallisation first from hot THF then acetone at −18° C. to give 12(i) as a white crystalline solid (360 mg, 66% yield).

3-[4-(3,5,5,8,8-Pentamethyl-5,6,7,8-tetrahydronaphthalen-2-yl)-phenyl]-acrylic acid methyl ester 12(i) (R=Me, R'=Me)

Pd(dppf)Cl$_2$ (23 mg, 0.028 mmol), 5,5-dimethyl-2-(3,5,5,8,8-pentamethyl-5,6,7,8-tetrahydronaphthalen-2-yl)-[1,3,2]dioxaborinane 3a (R=Me) (0.20 g, 0.64 mmol), K$_3$PO$_4$.2H$_2$O (0.29 g, 1.16 mmol) and 4-(3-bromo-phenyl)-acrylic acid methyl ester (0.14 g, 0.58 mmol) were placed in a thick walled glass tube fitted with a Young's tap along with degassed DMF (10 mL) and H$_2$O (2 mL) in a dry, N$_2$ filled, glovebox. The mixture was heated at 80° C. until GCMS analysis showed the reaction to be complete (2 d). Dilute HCl$_{(aq.)}$ (2 mL) was added and the mixture was extracted with Et$_2$O (3×10 mL). The organic phase was washed with dilute HCl$_{(aq.)}$ (3×10 mL), dried over MgSO$_4$ and concentrated in vacuo. The mixture was filtered through a silica plug with hexane and then 10% DCM/hexane and the solvent was removed in vacuo. Recrystallisation from hot EtOH gave the product 12(i) (R=Me, R'=Me) as a fluffy, white powder (0.17 g, 80%); mp 152-153.

3-[3-(3,5,5,8,8-Pentamethyl-5,6,7,8-tetrahydronaphthalen-2-yl)-phenyl]-acrylic acid methyl ester 12(ii) (R=Me, R'=Me)

Pd(dppf)Cl$_2$ (23 mg, 0.028 mmol), 5,5-dimethyl-2-(3,5,5,8,8-pentamethyl-5,6,7,8-tetrahydronaphthalen-2-yl)-[1,3,2]dioxaborinane 3a (R=Me) (0.2 g, 0.64 mmol), K$_3$PO$_4$.2H$_2$O (0.29 g, 1.16 mmol) and 3-(3-bromophenyl)acrylic acid methyl ester (0.14 g, 0.54 mmol) were placed in a thick walled glass tube fitted with a Young's tap along with degassed DMF (10 mL) and H$_2$O (2 mL) in a dry, N$_2$ filled, glovebox. The mixture was heated at 80° C. until GCMS analysis showed the reaction to be complete (2 d). Dilute HCl$_{(aq.)}$ (2 mL) was added and the mixture was extracted with Et$_2$O (3×10 mL). The organic phase was washed with dilute HCl$_{(aq.)}$ (3×10 mL), dried over MgSO$_4$ and concentrated in vacuo. The mixture was filtered through a silica plug with hexane and then 10% DCM/hexane and the solvent was removed in vacuo. Recrystallisation from hot EtOH gave the product 12(ii) (R=Me, R'=Me) as a fluffy, white powder (0.17 g, 83%); mp 121-122.

Compound 12(ii) (R=H, R'=H)

In a nitrogen atmosphere, 3a (534 mg, 1.7 mmol), 3-bromocinnamic acid (406 mg, 1.8 mmol), Pd(PPh$_3$)$_4$ (57.8 mg, 50 μmol) and Ba(OH)$_2$.8H$_2$O (1.25 g, 4.0 mmol) were dissolved in a degassed mixture of N,N-dimethylacetamide/purified water (5:1, 17 ml). The solids did not dissolve completely. The reaction was heated at 80° C. in a sealed tube for 3 days when the reaction was quenched with dilute hydrochloric acid (2 ml) and extracted with DCM (3×20 ml). The organic phase was washed with brine (1×10 ml) and dilute hydrochloric acid (5×20 ml); the combined aqueous washings were back-extracted with DCM (2×20 ml). The combined organic layers were dried over MgSO$_4$, filtered and concentrated in vacuo. Purification by silica gel chromatography (hexane:DCM, 1:1 as eluant), and recrystallisation first from EtOAc then acetone gave 11(ii) as a white crystalline solid (280 mg, 37% yield).

Compound 13 (R=H, R'=H)

In a nitrogen atmosphere, 3a (532 mg, 1.7 mmol), 6-bromo-2-naphthoic acid (439 mg, 1.7 mmol), Pd(PPh$_3$)$_4$ (58.9 mg, 51 μmol) and Ba(OH)$_2$.8H$_2$O (1.25 g, 4.0 mmol) were dissolved in a degassed mixture of N,N-dimethylacetamide/purified water (5:1, 17 ml). The solids did not dissolve completely. The reaction was heated at 80° C. in a sealed tube for 3 days when the reaction was quenched with dilute hydrochloric acid (15 ml) and extracted with EtOAc (3×50 ml). The organic phase was washed with water (3×20 ml); the combined aqueous washings were back-extracted with EtOAc (2×50 ml). The combined organic layers were dried over MgSO$_4$, filtered and concentrated in vacuo. The crude product was filtered through a silica gel pad (eluant=EtOAc). Recrystallisation from acetone at −20° C. gave four crops of 13 (250 mg, 41% yield) as colourless crystals.

3',5',5',8',8'-Tetramethyl-5',6',7',8'-tetrahydro-2,2'] binaphthalenyl-6-carboxylic acid methyl ester 13 (R=Me, R'=Me)

Pd(dppf)Cl$_2$ (23 mg, 0.28 mmol), 5,5-dimethyl-2-(3,5,5,8,8-pentamethyl-5,6,7,8-tetrahydronaphthalen-2-yl)-[1,3,2]dioxaborinane 3a (R=Me) (0.20 g, 0.64 mmol), K$_3$PO$_4$.2H$_2$O (0.29 g, 1.16 mmol) and 6-bromo-naphthalene-2-carboxylic acid methyl ester (0.15 g, 0.58 mmol) were placed in a thick walled glass tube fitted with a Young's tap along with degassed DMF (10 mL) and H$_2$O (2 mL) in a dry, N$_2$ filled, glovebox. The mixture was heated at 80° C. until GCMS analysis showed the reaction to be complete (2 d). Dilute HCl$_{(aq.)}$ (2 mL) was added and the mixture was extracted with Et$_2$O (3×10 mL). The organic phase was washed with dilute HCl$_{(aq.)}$ (3×10 mL), dried over MgSO$_4$ and concentrated in vacuo. The mixture was filtered through a silica plug with hexane and then 10% DCM/hexane and the solvent was removed in vacuo. Recrystallisation from hot EtOH gave the product 13 (R=Me, R'=Me) as a fluffy, white powder (0.19 g, 84%); mp 162-163.

Example 2

Determination of Physical and Chemical Stability

Taking into account that naturally occurring retinoids are sensitive and isomerise, we designed, synthesised and purified a number of synthetic retinoid derivatives as described herein, that display improved stability and similar biological activity. We have evaluated the biological activity of these molecules on different types of mammalian stem cell and their ability to modulate the differentiation of these cells.

In order to test the sensitivity of the natural retinoids, 10 mM samples in either DMSO or deuterochloroform were exposed to either 37° C., laboratory light (approximately 500 lux), white light (approximately 1250 lux) or UV light. Upon isomerisation HNMR spectra of samples were taken and compared to HNMR spectra of pure samples. The % peak intensities from the HNMR spectra were used to quantify levels of the different retinoic acids and any other compounds that may be present.

Retinoic Acids Isomerised at 37° C.

Temperature sensitivity was tested by placing solutions of retinoic acids in a 37° C. water bath for varying time lengths. After 1 hour at 37° C. approximate levels of the initial retinoic acid were 85% for a 13CRA sample and 100% for an ATRA sample. This decreased to 73% for a 13CRA sample and 86% for an ATRA sample after 24 hours.

Samples of ATRA and 13CRA, were left at room temperature for 1 week. The degraded solution of 13CRA contained around 78% 13CRA. The solution of ATRA was more stable and still contained 94% ATRA. All of the above experiments highlight retinoic acids inherent instability, not only in light, but also at 37° C. and even at room temperature.

Photoisomerisation of Retinoic Acids

The sensitivity of retinoic acids to light was tested by placing samples of ATRA, 9CRA and 13CRA in one of three lighting conditions for varying lengths of time. Samples were exposed to either normal laboratory light conditions, white light or UV light. HNMR spectra were then compared to those of pure samples.

Laboratory Light

Figure 2:
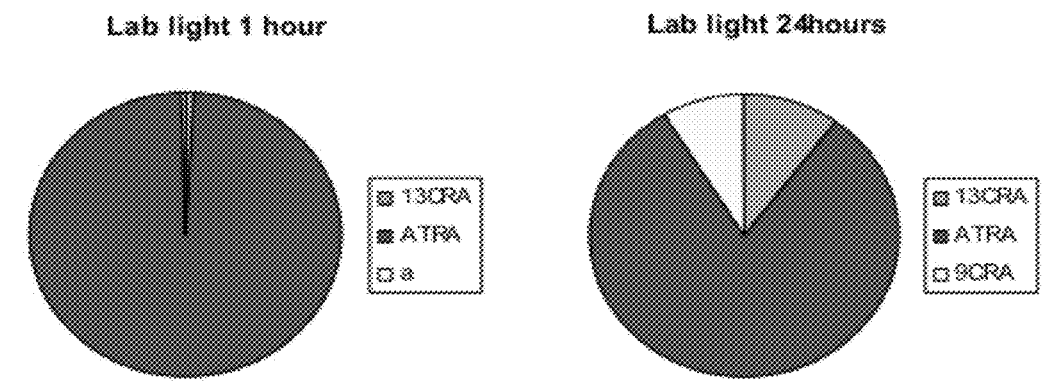
FIG. 2 shows the relative levels of the natural retinoids in samples of ATRA exposed to 1 hour (left) and 24 hours (right) laboratory light conditions (in November or December)

The relative ratios of the natural retinoic acid isomers found in samples of ATRA and 13CRA isomerised in lab light for 1 hour and 24 hours can be seen in FIGS. 1 and 2. The new peaks in HNMR spectra increased in size, and so levels of isomerisation products increased over 24 hours but not to any great extent. ATRA appears to be marginally more stable than 13CRA, especially up to 1 hour exposure.

Sunlight

Figure 3:
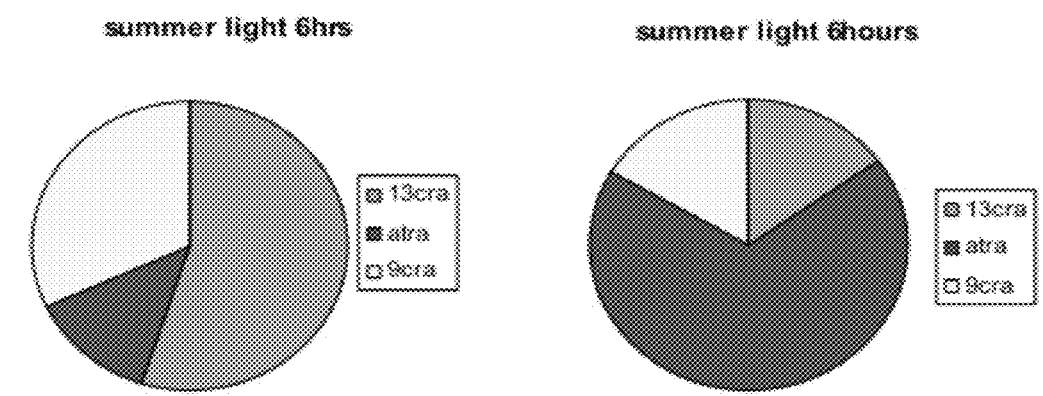
FIG. 3 shows the relative levels of the natural retinoids in samples of 13CRA (left) and ATRA (right) exposed to 6 hours of laboratory light conditions (in March). Samples were in direct sunlight.

Results in FIG. 3 are vastly different from those in FIGS. 1 and 2, retinoids isomerised for 6 hours in sunlight show a far greater extent of degradation. The only samples to show more degradation over the course of the investigation were samples exposed to UV light for 12 hours. Levels of 9CRA appear to have increased the most in both samples, although significantly more in the 13CRA sample. Many other compounds could be seen in the HNMR.

UV Light

Figure 4:
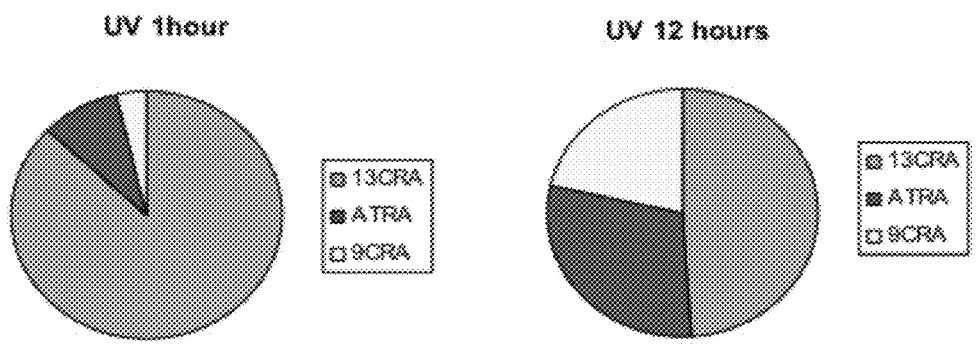
FIG. 4 shows the relative levels of the natural retinoids in samples of 13CRA exposed to 1 hour (left) and 12 hours (right) of UV light.
Figure 5:
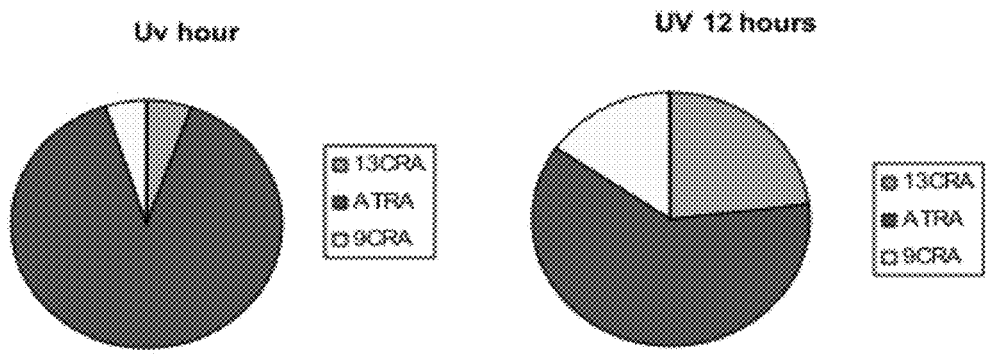
FIG. 5 shows the relative levels of the natural retinoids in samples of ATRA exposed to 1 hour (left) and 12 hours (right) UV light.

FIGS. 4 and 5 show the relative ratios of the natural retinoic acids found in samples of ATRA and 13CRA isomerised in UV light for 1 hour and 12 hours. ATRA and 13CRA become rapidly degraded over 12 hours. In contrast to the samples shown in FIG. 3, levels of ATRA have increased the most in samples shown in FIG. 4. Levels of 13CRA have increased the most in samples shown in FIG. 5. This difference indicates that exposure to a wider spectrum of wavelengths favours isomerisation at the $C_9$-$C_{10}$ bond, whereas a narrower range of light at a shorter wavelength tends appears to favour isomerisation at the $C_{13}$-$C_{14}$ position, either from the all-trans to the 13-cis configuration or from the 13-cis back to the all-trans configuration.

White Light

Levels of ATRA were found to decrease from 100% to 76% after 1 hour exposure to white light, 43% after 6 hours and 21% after 24 hours (data not shown). Again, the rate of degradation slows significantly after 6 hours.

Previous research into retinoic acid isomerisation has identified the relative concentrations of isomers for a sample of ATRA in ethanol exposed to white light for 30 minutes, to be ATRA 25%, 9CRA 10%, 11CRA 10%, 13CRA 30%, 9, 13-dicis RA 5% and an unidentified compound 20% (Giguere V. Endocrine Reviews, 1994, 15, 61-70). These isomers are believed to have reached a photostationary state. Samples isomerised in this investigation, have identified at least 9 isomerisation products including the natural retinoic acids.

Synthetic Retinoids

Samples of synthetic retinoids 12(ii), 12(i) and 13 were exposed to 1 hour of laboratory light, 1 hour of white light and 1 hour of UV light. HNMR spectra from samples exposed to lab light and white light were identical to those of pure compounds. No sign of decomposition was observed after 1 hour of lab light or white light. Samples of 12(ii) and 12(i) showed minor degradation after exposure to UV light. 13 showed no signs of degradation. UV light is emitted at a frequency likely to excite the conjugated double bond region of these synthetic retinoids, resulting in the slight degradation observed. 12(ii) and 12(i) were stable under laboratory light and white light. 13 was stable when exposed to all forms of light. Synthetic retinoids proved to be far more stable than their natural counterparts.

Figure 6:
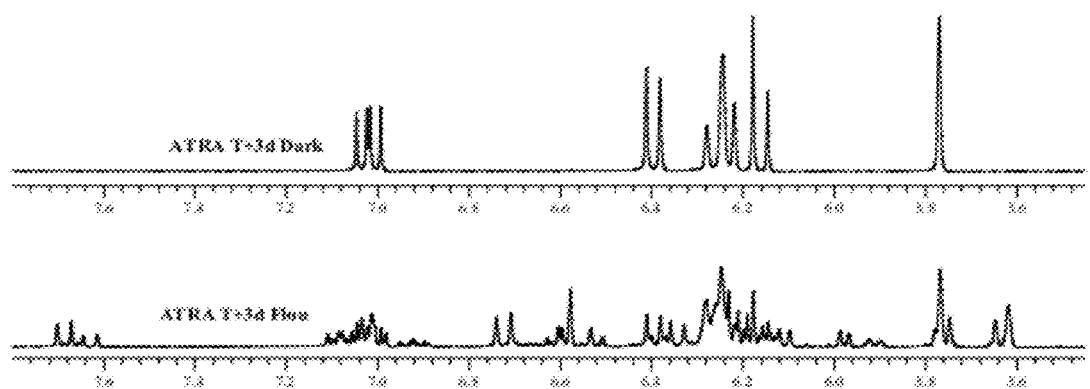
FIG. 6 $^1$H NMR (500 MHz) spectrum (d 5.40-7.80) of ATRA in $D_6$-DMSO in a glass NMR tube after 3 days in the dark under air (top), versus 3 days exposure to fluorescent light (bottom).
Figure 7:
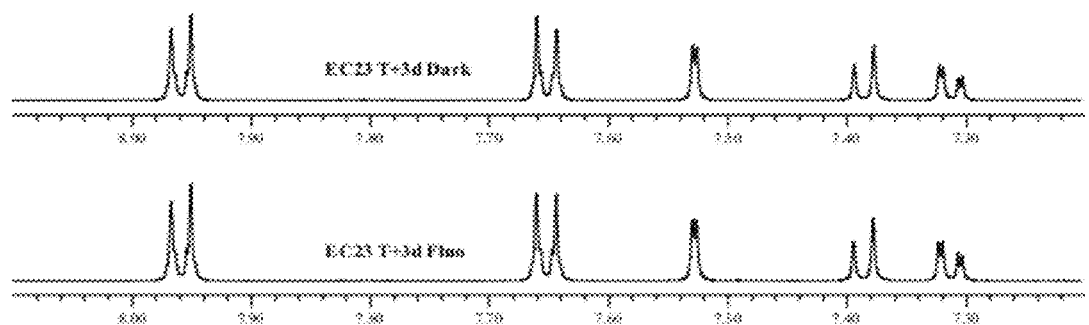
FIG. 7 $^1$H NMR (500 MHz) spectrum (d 7.20-8.10) of EC23 (10a(i) (R'=H)) in $D_6$-DMSO in a glass NMR tube after 3 days in the dark under air (top), versus 3 days exposure to fluorescent light (bottom).

In order to study the relative stability of certain synthetic retinoids versus the natural systems, solutions of each were exposed to different environmental conditions and then studied by NMR. FIGS. 6 and 7 clearly show that ATRA is reasonably stable over 3 days in the dark in air in DMSO, however, a exposure to fluorescent light causes 63% isomerisation and degradation, I only 37% remains after 3 days by NMR. In contrast, synthetic retinoid 10a(i) (R'=H) is completely stable under the same conditions.

Example 3

Determination of Biological Activity

The biological activity of compounds 6, 10, 11, 12 and 13 were determined by exposing these molecules at various concentrations to different mammalian stem cell systems, namely (1) human pluripotent stem cells; and (2) rat adult neuroprogenitor cells.

Compound Testing on Human Pluripotent Stem Cells

Tissue development by human pluripotent stem cells closely resembles that which occurs during normal embryogenesis in utero and this cell system is a proven and accepted model of cell differentiation (Przyborski et al, Stem Cells Dev., 2004, 13:400-408).

The expression of cell surface antigens that are known to change as these stem cells commit to differentiate, was assessed by flow cytometry. Test molecule 10a(i) induced the suppression of the stem cell markers TRA-1-60 and SSEA-3 whilst antigens associated with differentiated tissues, A2B5 and VINIS-53, showed marked increases in expression over the 14 day test period. These changes were directly comparable to those induced by non-isomerised ATRA.

Test compound 10a(i) induced the formation of morphologically identifiable neurons which was confirmed by immunocytochemistry. Test compound 10a(ii) is of a different molecular structure and induced an alternative path of cellular differentiation resulting in the formation of epithelial cells. Neurons were not identified in cultures treated with compound 10a(ii).

Test compound 10a(i) showed essentially identical behaviour to natural ATRA which is known to be an essential biological agent in cell development. Indeed, it is predicted that in DMSO solution under normal ambient conditions (in normal air, room temperature, natural and fluorescent light), and based on their structure, these two compounds would remain stable for many weeks, which is the case in preliminary results. In sharp contrast, all the retinoic acid stereoisomers under go rapid isomerisation to give mixtures of the three main isomers, with one, as yet unidentified (by NMR and HPLC), additional isomer, together with degradation products. Compound 10a(i) is directly super-imposable on ATRA, whereas 10a(ii) is similarly closely related to the two important cis-stereoisomers, resulting in the observed conservation of biological activity.

Retinoid 11a(ii) had striking biological activity, and the cultures grown under its presence halted proliferation almost instantly. In addition, the retinoid displayed potent cytotoxicity towards the TERA2.cl.SP12 cells, killing them within 4 days.

Figure 8:
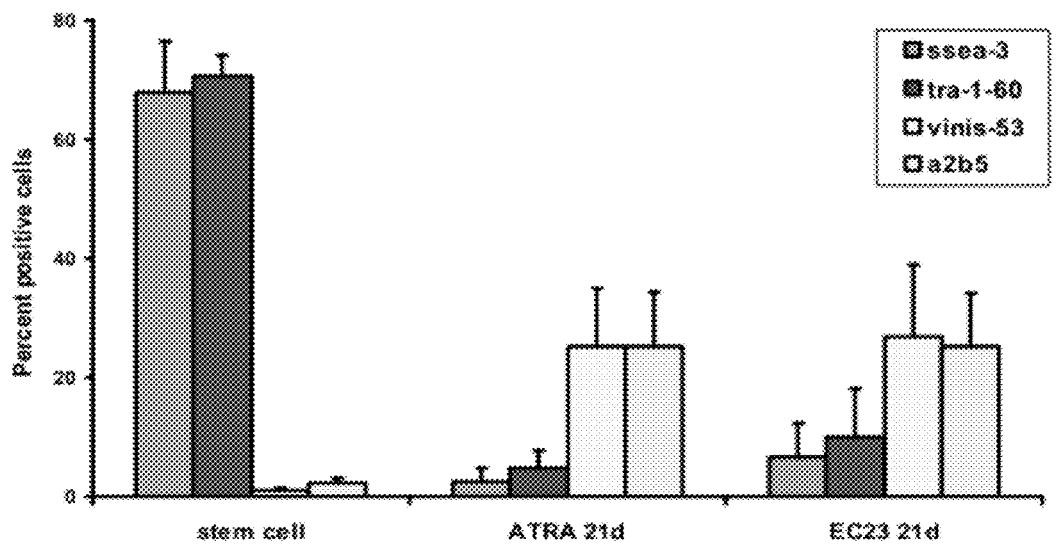
FIG. 8 Flow cytometric analysis of cell surface antigen expression for markers of stem cells (ssea-3, tra-1-60) and differentiated derivatives (vinis-53, a2b5) when cultures of human pluripotent embryonal carcinoma stem cells (TERA2.SP12) exposed to either 10 μM ATRA or 10 μM EC23 (10a(i) (R'=H)).
Figure 9:
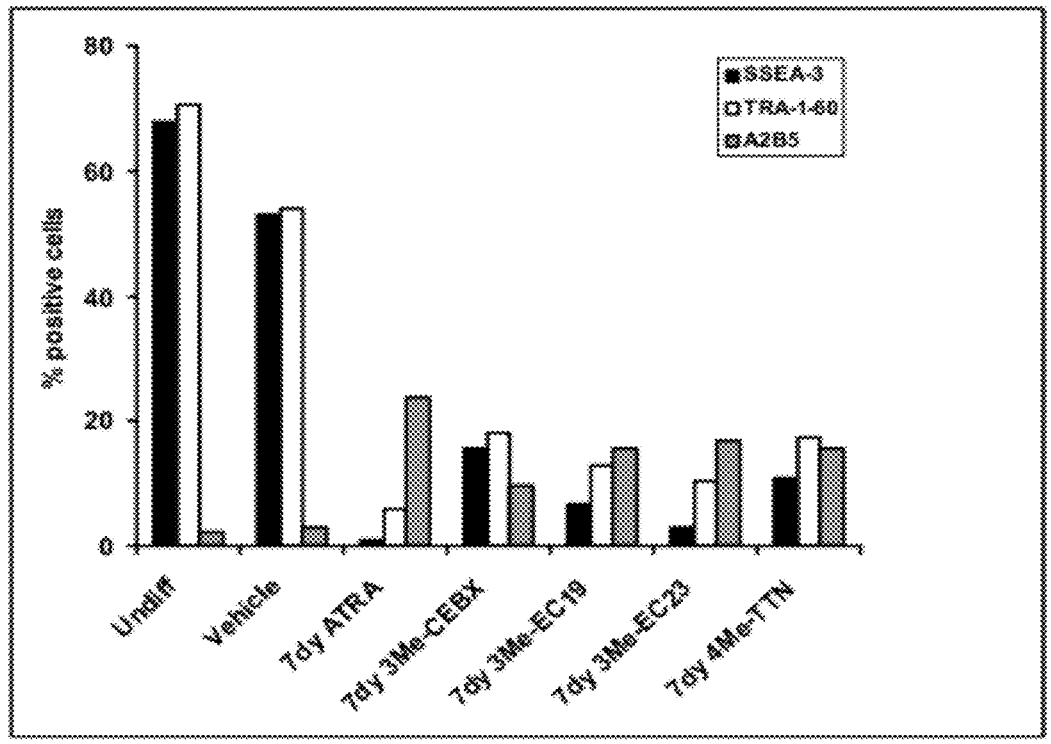
FIG. 9 Flow cytometric analysis of cell surface antigen expression on human pluripotent TERA2.cl.SP12 embryonal carcinoma stem cells (undiff) and their differentiated derivatives after 7 days exposure to either ATRA; 3Me-CEBX (12); 3Me-EC19 (10b(ii) R'=H); 3Me-EC23 (10b(i) (R'=H)); 4Me-TTN (6b(i)(R'=H)); all used at 1 μM. DMSO was used as a vehicle control.

Flow cytometry was also used to assay for the effect(s) of compounds 6, 10 and (FIGS. 8 and 9). These compounds induced the suppression of the stem cell markers TRA-1-60 and SSEA-3 whilst antigens associated with differentiated tissues, A2B5 and VINIS-53, showed marked increases in expression over the test period. These changes were directly comparable to those induced by non-isomerised ATRA. These data clearly indicate that stem cells respond to the test molecules by the induction of cell differentiation in a predictable manner.

Analysis of protein expression by immunofluorescent microscopy showed alternative pathways of cell differentiation induced by exposure to either ATRA, compound EC23 (10a(i)) or EC19 (10a(ii)) (10 µM) for 21 days. ATRA induced the formation of neurons (positive for the neural markers nestin, Tuj-1 and NF200) and numerous epithelial plaques (p) as indicated by islands of flat cells stained with cytokeratin-8. Exposure to EC23 produced very few, if any, epithelial plaques and resulted in cultures more homogenous in appearance consisting primarily of cells undergoing neuronal differentiation. This was further demonstrated by strong expression for nestin, especially in neural rosettes (nr) indicative of neuro-proliferative centres. In contrast, EC19 induced the formation of very few neurons with nestin staining reduced and the presence of only a few cells immuno-positive for Tuj-1 and NF200. However, large numbers of cytokertin-8 positive epithelial plaques were noted.

Compound Testing on Adult Neuroprogenitor Cells

The biological activity of the synthetic retinoid EC23 (10a(i)) was also evaluated by exposing it to neuroprogenitor cells derived from the adult rat hippocampus. These cells are multi-potent and differentiate in response to non-isomerised ATRA and primarily form neurons that produce an elaborate network of neurites. The same cells exposed to test compound 10a(i) also differentiate into well-defined neurons. Immunocytochemical staining for the marker β-tubulin-III was used to confirm neuronal identity (data not shown).

The invention claimed is:

1. A method of using a retinoid compound to control cell differentiation, said method comprising contacting said cell with an amount of said compound sufficient to control said cell differentiation, wherein the compound is of the formula (V),

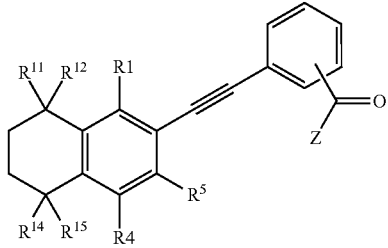

Formula V wherein
- $R^1$, $R^4$ and $R^5$ are each independently selected from hydrogen, $R^6$, hydrocarbyl optionally substituted with 1, 2, 3, 4 or 5 $R^6$, and —(CH$_2$)k-heterocyclyl optionally substituted with 1, 2, 3, 4 or 5 $R^6$;
- each $R^6$ is independently selected from halogen, trifluoromethyl, cyano, nitro, oxo, =NR$^7$, —OR$^7$, —C(O)R$^7$, —C(O)OR$^7$, —OC(O)R$^7$, —S(O)$_l$R$^7$, —N(R$^7$)R$^8$, —C(O)N(R$^7$)R$^8$, —S(O)$_l$N(R$^7$)R$^8$ and R$^9$;
- $R^7$ and $R^8$ are each independently hydrogen or $R^9$;
- $R^9$ is selected from hydrocarbyl and —(CH$_2$)$_k$-heterocyclyl, either of which is optionally substituted with 1, 2, 3, 4 or 5 substituents independently selected from halogen, cyano, amino, hydroxy, $C_{1-6}$ alkyl and $C_{1-6}$ alkoxy;
- k is 0, 1, 2, 3, 4, 5 or 6;
- l is 0, 1 or 2;
- $R^{11}$, $R^{12}$, $R^{14}$ and $R^{15}$ are each independently selected from hydrogen, $R^6$, hydrocarbyl optionally substituted with 1, 2, 3, 4 or 5 $R^6$, and —(CH$_2$)$_k$-heterocyclyl optionally substituted with 1, 2, 3, 4 or 5 $R^6$; and
- Z is selected from —OH and NHOH; and
- wherein any one or more of the aliphatic and the aromatic groups of formula V may optionally be substituted with one or more $R^6$ groups;
- or a salt thereof.

2. The method according to claim 1, wherein the compound is of the formula (IX)

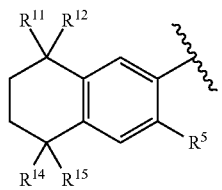
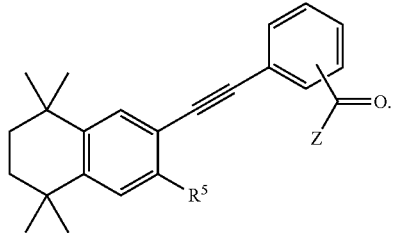

Formula (IX)

3. The method according to claim 1, wherein $R^{11}$, $R^{12}$, $R^{14}$ and $R^{15}$ are each independently hydrogen or C1 to C6 alkyl.

4. The method according to claim 2, wherein $R^5$ is hydrogen or methyl.

5. The method according to claim 1 wherein the cell is a stem cell.

6. The retinoid compound as defined in claim 1.

7. The method of controlling cell differentiation comprising contacting cells with a compound of claim 1.

8. The method according to claim 2, wherein Z is OH.

9. The method according to claim 5, wherein the cell is not a totipotent stem cell.

10. The method according to claim 5, wherein the stem cell is selected from the group consisting of: haemopoietic stem cell, neural stem cell, bone stem cell, muscle stem cell, mesenchymal stem cell, epithelial stem cell, ectodermal stem cell, mesodermal stem cell, and endodermal stem cell.

11. The method according to claim 1, wherein the method is in vitro and comprises the steps of:
   i) forming a preparation of stem cells in a cell culture medium suitable for maintaining said stem cells wherein said culture medium comprises a compound according to formula V; and
   ii) cultivating said stem cells in conditions that allow their differentiation into at least one differentiated cell type.

12. The method as claimed in claim 11, wherein said method takes place in the presence of visible light and/or UV light.

* * * * *